United States Patent
Zhang et al.

(10) Patent No.: US 9,260,473 B2
(45) Date of Patent: Feb. 16, 2016

(54) BIVALENT MULTIFUNCTIONAL LIGANDS TARGETING Aβ OLIGOMERS AS TREATMENT FOR ALZHEIMER'S DISEASE

(75) Inventors: Shujin Zhang, Richmond, VA (US); Tai Liang Guo, Athens, GA (US)

(73) Assignee: Virginia Commonwealth University, Richmond, VA (US)

( * ) Notice: Subject to any disclaimer, the term of this patent is extended or adjusted under 35 U.S.C. 154(b) by 381 days.

(21) Appl. No.: 13/810,826

(22) PCT Filed: Jul. 14, 2011

(86) PCT No.: PCT/US2011/043980
§ 371 (c)(1),
(2), (4) Date: Jan. 17, 2013

(87) PCT Pub. No.: WO2012/012257
PCT Pub. Date: Jan. 26, 2012

(65) Prior Publication Data
US 2013/0156705 A1 Jun. 20, 2013

Related U.S. Application Data

(60) Provisional application No. 61/365,442, filed on Jul. 19, 2010.

(51) Int. Cl.
| | | |
|---|---|---|
| *A61K 31/56* | (2006.01) | |
| *A61K 31/575* | (2006.01) | |
| *C07J 43/00* | (2006.01) | |
| *A61K 31/4192* | (2006.01) | |
| *A61K 49/00* | (2006.01) | |
| *G01N 33/68* | (2006.01) | |

(52) U.S. Cl.
CPC ............ *C07J 43/003* (2013.01); *A61K 31/4192* (2013.01); *A61K 31/56* (2013.01); *A61K 31/575* (2013.01); *A61K 49/0052* (2013.01); *G01N 33/6896* (2013.01)

(58) Field of Classification Search
CPC .. A61K 31/575; A61K 31/56; A61K 31/4192
USPC .......................................... 514/176; 424/9.6
See application file for complete search history.

(56) References Cited

U.S. PATENT DOCUMENTS

| | | |
|---|---|---|
| 7,378,248 B2 | 5/2008 | Lorens |
| 2007/0213512 A1 | 9/2007 | Krafft |
| 2008/0113444 A1 | 5/2008 | Pray |
| 2008/0261819 A1 | 10/2008 | Lorens |
| 2009/0104629 A1 | 4/2009 | Fiala |
| 2010/0028357 A1 | 2/2010 | Matsubara |

OTHER PUBLICATIONS

Richard Golden. Dementia and Alzheimer's Disease, Indications, Diagnosis, and Treatment. Clinical & Health Affairs. Minnesota Medicine. Jan. 1995 vol. 78 pp. 25-29.*
Laabich et al. Neuroprotective effect of AIP on N-methyl-D-aspartate-induced cell death in retinal neurons. Molecular Brain Research 85 (2000) 32-40.*
Prasad,et al., "Risk Factors for Alzheimer's Disease: Role of Multiple Antioxidants, Non-Steroidal Anti-inflammatory and Cholinergic Agents Alone or in Combination in Prevention and Treatment", Journal of the American College of Nutrition, 2002, pp. 506-522, vol. 21, No. 6, American College of Nutrition, USA.
Lenhart et al., ""Clicked" Bivalent Ligands Containing Curcumin and Cholesterol as Multifunctional A[beta] Oligomerization Inhibitors: Design, Synthesis, and Biological Characterization", Journal of Medicinal Chemistry, Jul. 28, 2010, pp. 6198-6209, vol. 53.

* cited by examiner

*Primary Examiner* — Jennifer M Kim
(74) *Attorney, Agent, or Firm* — Whitham, Curtis, Christofferson & Cook, P.C.

(57) ABSTRACT

Bivalent multifunctional Aβ oligomerization inhibitors (BMAOIs) that target multiple risk factors involved in Alzheimer's disease are provided. The BMAOIs are useful for the treatment and/or prevention of Alzheimer's disease, as well as for diagnostic imaging of Aβ plaques in brain tissue. The BMAOIs comprise i) an Aβ oligomer (ApO)-inhibitor moiety which may have antioxidant activity (e.g. curcumin, curcumin derivatives, curcumin hybrids, resveratrol, etc.); ii) a cell membrane/lipid raft (CM/LR) anchoring moiety (e.g. cholesterol, cholesterylamine, a steroid, etc.); and iii) a spacer or linker moiety that stably links i) and ii) together.

12 Claims, 16 Drawing Sheets

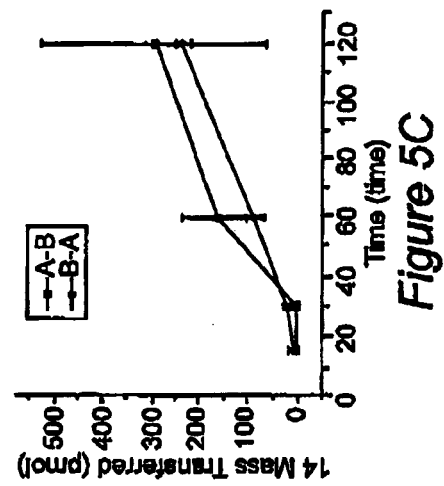
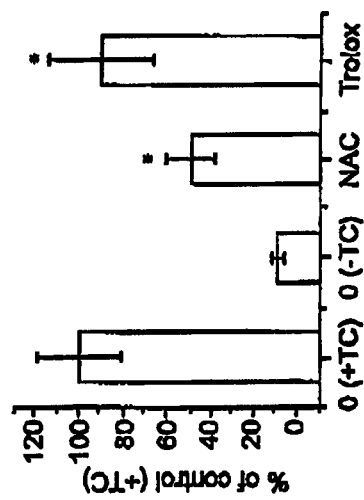
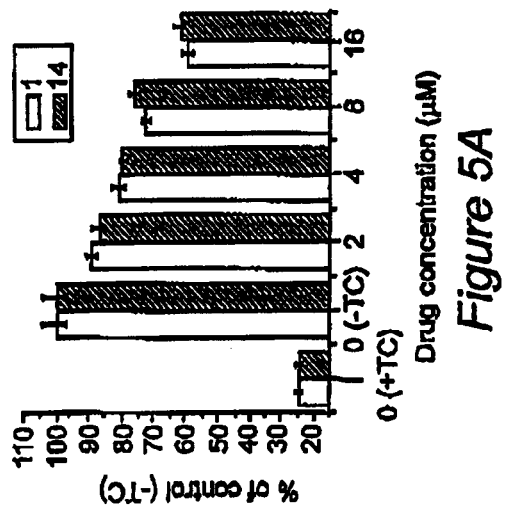
Figure 5C
Figure 5B
Figure 5A

Anti-ADDL staining of Aβ plaques in the adjacent brain tissue of TgCRND8 mouse 14 staining of Aβ plaques in the brain tissue of TgCRND8 mouse

BIVALENT MULTIFUNCTIONAL LIGANDS TARGETING Aβ OLIGOMERS AS TREATMENT FOR ALZHEIMER'S DISEASE

STATEMENT OF GOVERNMENT INTEREST

This invention was made with government support under contract number R01 AG041161 awarded by the National Institutes of Health. The government has certain rights in the invention.

BACKGROUND OF THE INVENTION

1. Field of the Invention

The invention generally relates to compounds that are useful for the treatment and/or prevention of Alzheimer's disease, and for diagnostic imaging of Aβ plaques. In particular, the invention provides novel bivalent multifunctional Aβ oligomer inhibitors (BMAOIs) that target multiple risk factors involved in Alzheimer's disease (e.g. Aβ oligomers, oxidative stress, biometals and cell membrane/lipid rafts). The BMAOIs comprise i) a multifunctional Aβ oligomer inhibiting moiety; ii) a cell membrane/lipid raft (CM/LR) anchoring moiety; and iii) a spacer moiety that links i) and ii) together.

2. Background of the Invention

Alzheimer's disease (AD) is a devastating neurodegenerative disease and is the most common cause of dementia. The amyloid-β (Aβ) hypothesis has long been recognized as the main theory in the development of Alzheimers disease (AD) and recently emerging evidence indicate that small, soluble oligomers (AβOs) are responsible for disruption of neuronal synaptic plasticity and the resulting early cognitive impairment associated with AD. Studies of brain samples from AD patients also confirmed the correlation of AβOs with the severity of dementia. Most recently, new evidence has indicated that soluble AβOs can up-regulate tau pathology, which further highlights the importance of AβOs in the pathogenesis of AD. Different types of soluble AβOs have been described using various resources. The heterogeneity of AβOs demonstrated so far might suggest that these multiple Aβ assemblies exert their neurotoxicity in a variety of ways such as selective uptake and internalization of AβOs through endocytic process demonstrated in cell models, induction of apoptosis, formation of ion channels, dyshomeostasis of biometals, and mishandling of calcium, among others. Despite the heterogeneity of the underlying mechanisms for Aβ's neurotoxicity, one point of consensus remains clear: the requirement of AβOs. Although some studies have indicated that protofibrils might be intermediates of the final mature fibrils, recent studies have suggested that Aβ oligomerization and fibril formation result from independent pathways. Collectively, these findings suggest AβOs as critical contributors in the development of AD pathology, thus providing compelling support for developing AβO inhibitors as therapeutic agents for the treatment of AD.

Besides the characteristic Aβ plaques and tangles, a loss of biometal homeostasis and increased oxidative damage are two other features consistently found in the brains of AD patients. High concentrations of Cu, Zn and Fe have been found within Aβ deposits in both AD human brains and transgenic mouse models. Furthermore, Aβ has been demonstrated to be a metalloprotein that binds to biometals and Aβ interactions with Cu, Zn and Fe can further induce Aβ aggregation and oligomerization. Particularly, Zn and Cu can readily precipitate AβOs but not Aβ monomers. The fact that glutamatergic synapses release high concentrations of Cu and Zn during neurotransmission may explain why AβOs are the major toxic species that impair synaptic plasticity. Oxidative stress is another early event of AD implicated as an important mediator in the etiology of AD. Transgenic mice studies have showed a correlation of increased oxidative stress and Aβ accumulation. Furthermore, secondarily to Aβ binding to biometals and assembling into oligomers and fibrils, Aβ also reduces these metals to produce reactive oxygen species (ROS) that contributes to most types of oxidative damage noted in AD.

Based on the aforementioned theories, numerous strategies have been developed in the past decade as potential AD treatments. This includes secretase inhibitors, Aβ oligomerization/aggregation inhibitors, immunotherapy, metal-complexing agents, anti-oxidants and anti-inflammation agents (NSAIDs). However, the fact that very few of them moved to clinical trials and none of them has been approved by FDA suggests that targeting a single risk factor is not an ideal strategy for developing treatments for this multifaceted disease. The recent failure of AlzheMed (trimprosate), a small molecule of AβO inhibitor, in phase III confirms this point of view.

Although the mechanism of how nontoxic Aβ converts to the toxic AβOs remains elusive, a wealth of data has implicated the roles of neuronal cell membranes/lipid rafts (CM/LR) in the oligomerization and toxicity of Aβ. Once associated with the membranes, Aβ exhibits an enhanced rate of aggregation that is dependent on pH and metal ion and ganglioside interactions. Recently, evidence has also indicated that lipid rafts, a cell membrane microdomain enriched in cholesterol and sphingolipids, may play important roles in Aβ precursor protein (APP) processing and Aβ oligomerization. Current studies of lipid rafts are mainly based on the isolation of detergent-resistant membrane (DRM) using different detergents like Triton X-100.30 Although it is still debated whether DRM are the same as "real" lipid rafts, studies using DRM analysis have revealed that rafts are involved in a variety of cell functions. Lipid rafts have been demonstrated to accelerate the cell membrane binding of Aβ. On the other hand, destruction of lipid rafts affects Aβ membrane binding and protects cells from Aβ toxicity. Most recently, it has been demonstrated that lipid rafts isolated from rat brain tissue and ganglioside-rich C2C12 cells can accelerate the oligomerization of Aβ. Furthermore, APP and its cleavage enzymes (β- and γ-secretases), monomeric Aβ and AβOs have all been identified in lipid rafts/DRM, suggesting that lipid rafts may be a critical platform for Aβ production and oligomerization. Additionally, biometals, such as Cu, have also been indicated to modulate the interaction of Aβ with membrane rafts. Altogether, it is apparent that CM/LRs are important regulators in AD development.

Even though the multifactorial nature of AD and the lack of a unified theory on its etiology have heretofore significantly stymied conventional drug discovery approaches, these difficulties may, however, present an opportunity by suggesting a more efficient and novel way to treat AD by targeting multiple contributors to AD etiology with a single molecule.

SUMMARY OF THE INVENTION

In order to overcome the limits posted by the traditional single-target based approach to the treatment of AD, herein we describe strategies for the design of bivalent multifunctional Aβ oligomerization inhibitors (BMAOIs) that target CM/LR and other factors involved in the etiology of AD. These BMAOIs contain i) a AβO-inhibitor pharmacophore that may also be multifunctional and accommodate additional anti-oxidation and metal chelation properties; and ii) a CM/LR anchor pharmacophore, the two components being linked by a spacer. The BMAOIs chaperone the multifunctional AβO-inhibitor moiety into close proximity to CM/LRs where Aβ oligomerization and Aβ/biometals interactions occur, thereby increasing the local concentration of the pharmacophores in the vicinity of CM/LRs. As a result, the accessibility of the BMAOIs and their ability to interfere with the multiple processes involved in the development of AD is greatly increased, and the clinical efficacy of the compounds described herein is improved over traditional single factor targeted compounds. Significantly, the BMAOIs are able to cross the blood brain barrier and thus exert their effects within the brain. It has also been discovered that, in some embodiments, the compounds are useful for fluorescent imaging of Aβ plaques as they retain the intrinsic fluorescence properties of the AβO-inhibitor, e.g. when the AβO-inhibitor is curcumin.

It is an object of this invention to provide a bivalent multifunctional Aβ oligomerization inhibitor (BMAOI) comprising i) a multifunctional Aβ oligomer (AβO-inhibitor moiety; ii) a cell membrane/lipid raft (CM/LR) anchor; and iii) a spacer moiety which forms a chemical linkage between the AβO-inhibitor moiety and the CM/LR anchor. In some embodiments, the AβO-inhibitor moiety is, for example, curcumin, resveratrol, or a hybrid molecule that comprises curcumin. For example, the hybrid molecule may comprise curcumin and melatonin. In some embodiments, the CM/LR anchor is, for example, cholesterol, a cholesterol derivative, or a steroid. The cholesterol derivative may be cholesterylamine, and the steroid may be diosgenin. In some embodiments, the spacer moiety is 21 atoms in length. In other embodiments, the AβO-inhibitor moiety is curcumin and the spacer moiety is chemically linked to carbon at position C4 of the curcumin. In some embodiments, the CM/LR anchor is cholesterol and the spacer moiety is chemically linked to O attached to (at) position C3 of the cholesterol. In other embodiments, the CM/LR anchor is cholesterylamine and the spacer moiety is chemically linked to N attached to/at position C3 of the cholesterylamine. In some embodiments of the invention, the AβO-inhibitor moiety has antioxidant activity and/or metal chelating properties.

The invention also provides a method of preventing or treating Alzheimer's disease (AD) in a patient in need thereof. The method comprises the step of administering to the patient a bivalent multifunctional Aβ oligomerization inhibitor (BMAOI) comprising i) an Aβ oligomer (AβO-inhibitor moiety; ii) a cell membrane/lipid raft (CM/LR) anchor; and iii) a spacer moiety which forms a chemical linkage between the AβO-inhibitor moiety and the CM/LR anchor. The BMAOI is administered in an amount sufficient to prevent or treat AD in the patient. In one embodiment of the invention, the bivalent multifunctional ligand is compound 14,

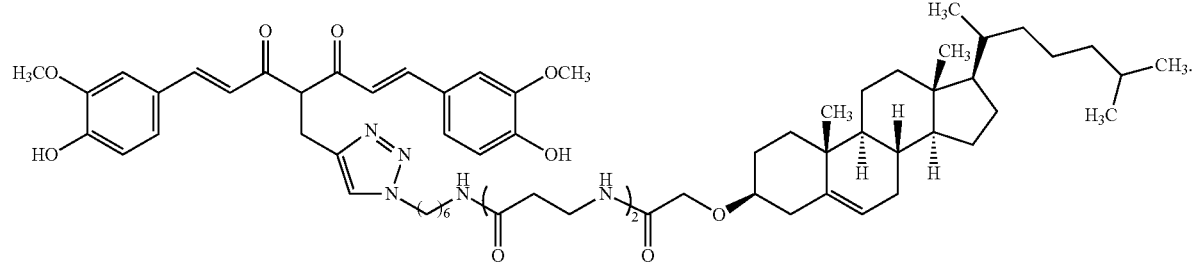

14

In another embodiment, the bivalent multifunctional ligand is compound 51,

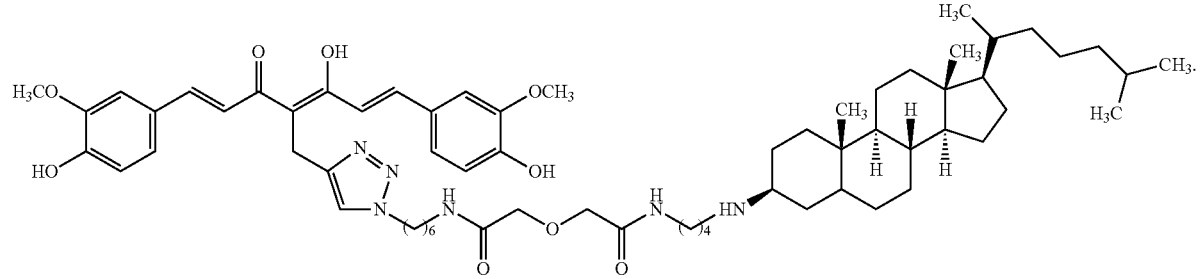

51

The invention also provides a method of imaging or visualizing β-amyloid (Aβ) plaques in brain tissue. The method comprises the steps of: A, exposing the brain tissue to at least one bivalent multifunctional Aβ oligomerization inhibitor (BMAOI) comprising i) a fluorescent Aβ oligomer (AβO-inhibitor moiety; ii) a cell membrane/lipid raft (CM/LR) anchor; and iii) a spacer moiety which forms a chemical linkage between the AβO-inhibitor moiety and the CM/LR anchor, the step of exposing being carried out under conditions that allow the at least one BMAOI to associate with Aβ plaques in the brain tissue; B, exposing the brain tissue to a source of electromagnetic radiation; and C, detecting fluorescence emitted from BMAOIs associated with Aβ plaques. In one embodiment, the bivalent multifunctional ligand is compound 14, tioned medium were analyzed by ELISA. Data were expressed as mean percentage of AβOs (n=4) with parallel DMSO cultures set at 100%. Error bars represent standard error of mean (SEM).

FIG. 4A-D. Protective effects of 14. A. MC65 cells were treated with 1 (curcumin) as a comparative standard or compound 14 at indicated concentrations under +TC or −TC conditions for 72 hrs. Cell viability was assayed by MTS assay. Data were expressed as mean percentage viability (n=6) with parallel +TC cultures set at 100% viability. Error bars represent SEM. B. All-trans-retinoic acid differentiated SH-SY5Y cells were treated with AβOs (1 μM) in the presence or absence of test compounds at indicated concentrations for 48 hrs. Cell viability was assayed by MTS assay. Data were expressed as mean percentage viability (n=6) with cultures without AβOs set at 100% viability. Error bars rep-

14

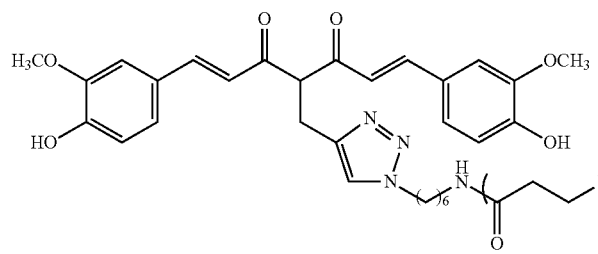
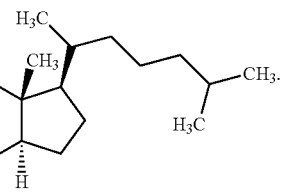

In another embodiment, the bivalent multifunctional ligand is compound 51, resent SEM. C. Effects of 14 (10 μM) on anti-CD3 antibody mediated splenocyte proliferation. D. Effects of 14 (10 μM)

51

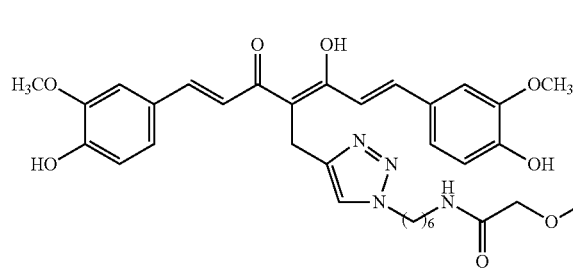

BRIEF DESCRIPTION OF THE DRAWINGS

FIG. 5A-C. Antioxidant effects and Caco-2 permeability of 14. A. MC65 cells were treated with 1 or 14 at indicated concentrations under +TC or −TC conditions for 24 hrs, then DCFH-DA (25 μM) was loaded and fluorescence intensity was analyzed at 485 nm (excitation) and 530 nm (emission). Data were presented as mean percentage of fluorescence intensity (n=5) with parallel −TC cultures set at 100%. Error bars represent SEM. B. MC65 protection was performed as described in FIG. 6A with NAC (8 mM) or Trolox (32 μM) (n=5). C. Caco-2 cells were plated on transwell filters. Test compounds (10 μM) were added to either the apical or basolateral side, then samples were analyzed by HPLC to determine flux (A-B: apical-to-basolateral; B-A: basolateral-to-apical) at indicated time points. Data were presented as mean (n=3)±SEM. *P<0.05 indicates significant differences from control group (−TC) analyzed by one-way ANOVA.

DETAILED DESCRIPTION

Figure 1:
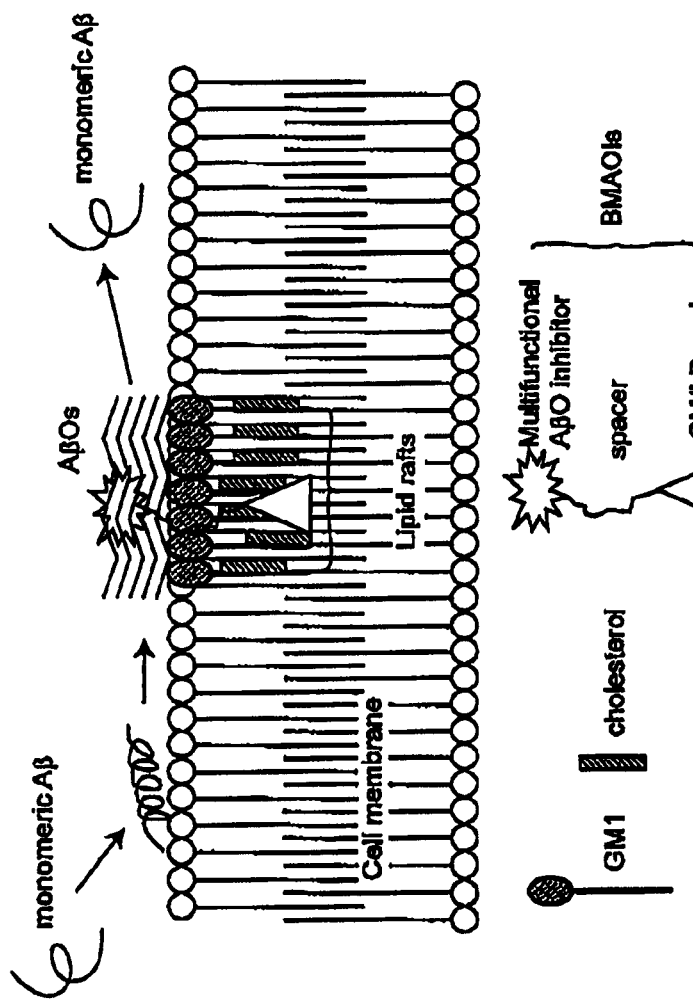
FIG. 1. BMAOIs strategy and design.

The invention provides BMAOI compounds that are useful for the treatment and/or prevention of Alzheimer's disease. The BMAOIs comprise three components: i) an AβO-inhibitor moiety; ii) a cell membrane/lipid raft (CM/LR) anchor; and iii) a spacer moiety which forms a chemical linkage between the AβO-inhibitor moiety and the CM/LR anchor. The AβO-inhibitor moiety may have intrinsic antioxidant activity, and may have metal chelating properties. The compounds of the invention are thus bivalent ligands that are capable of targeting multiple risk factors involved in Alzheimer's disease, for example, Aβ oligomers, oxidative stress, biometals and cell membrane/lipid rafts. In other words, activities such as disruption of Aβ oligomerization, prevention, of oxidation and biometal chelation and disruption of the development of large CM/LR networks are all contained within a single molecule. In addition, the BMAOIs may be fluorescent, e.g. when the AβO-inhibitor moiety is intrinsically fluorescent and the intrinsic fluorescence is retained in the BMAOI.

The compounds may be referred to herein as referred to as "ligands" because components i) and ii) are capable of interacting with or binding to other moieties. For example, the anchor component is capable of interacting with (e.g. undergoing hydrophobic interaction or association with) cell membranes and/or lipid rafts; and the AβO-inhibitor/antioxidant moiety is capable of interacting with at least one, and usually several, other moieties which have bearing on the development of AD, e.g. with metals and metal ions, with AβOs, and with various species which cause oxidation, e.g. various reactive oxygen species (ROS). Similarly, the compounds may be referred to as "bivalent" because of the presence of two unique components, each of which has an independent repertoire of biological activities.

The three components of the BMAOI compounds, which may be independently selected, are each described in detail below.

AβO-Inhibitor Moieties

The BMAOIs contain a moiety which is both capable of inhibiting Aβ oligomer formation and which, in preferred embodiments, displays antioxidant effects. By "capable of inhibiting Aβ oligomer formation" we mean that the agent or pharmacophore is capable of preventing, slowing, or in some cases even reversing the formation or polymerization of Aβ oligomers and/or assemblies in brain tissue. That is to say, the frequency of occurrence of Aβ oligomers in brain tissue and/or the amount or number of Aβ oligomers in brain tissue (or of other structures which are in turn formed from the aggregation of Aβ oligomers) is decreased at least by about 25% or more (e.g. by about 30, 35, 40, 45, 50, 55, 60, 65, 70, 75, 80, 85, 90, 95 or even 100% or more) in the presence of the agent, compared to the levels measured in the absence of the agent.

By "antioxidant" we mean a substance that reduces oxidative damage (damage due to oxygen species) such as that caused by free radicals and/or other reactive oxygen species (ROS), including molecules or ions formed by the incomplete one-electron reduction of oxygen. These reactive oxygen intermediates include singlet oxygen; superoxides; peroxides; hydroxyl radical; hypochlorous acid, etc.

Suitable examples of AβO-inhibitor/antioxidant agents for use as components of the BMAOIs include but are not limited to: various phytochemicals and natural products which are known to possess these two properties (e.g. curcumin, resveratrol, catechins, melatonin, etc.), as well as active derivatives and/or hybrids of these agents. Such substances may be isolated from natural sources, manufactured by organisms that naturally or are genetically engineered to produce them, or chemically synthesized. These agents also include hybrid molecules that contain essential or active parts of the AβO-inhibitor structures, for example, hybrid molecules of curcumin and melatonin, or other combinations.

In one exemplary embodiment of the invention, the AβO-inhibitor/antioxidant moiety is curcumin, or a curcumin derivative, or otherwise comprises curcumin. The chemical structure of curcumin is provided in FIG. 2, which depicts curcumin as compound 1. Alternatively, the moiety may be a curcumin derivative that still retains at least about 50% or more of the antioxidant and anti-AβO activity of curcumin; or a hybrid molecule composed of curcumin (or a curcumin derivative) that is chemically attached to another molecule of interest, the chemical linkage being formed in a manner that results in retention of at least about 50% or more of the anti-oxidant and anti-AβO activity of curcumin. Herein, this portion of the molecule may be referred to as the "curcumin moiety" or the "curcumin portion" of the ligand, and by other similar terms which are intended to encompass curcumin, curcumin derivatives and/or hybrid molecules which contain curcumin or a curcumin derivative.

Exemplary curcumin derivatives include but are not limited to: derivatives in which one or more hydroxyls are modified e.g. by the addition of other chemical groups such as dimethylamino, diethylamino, etc; as well as piperidine and peperazine, for example. Those of skill in the art will be familiar with which atoms of curcumin may be so modified, and with protocols for doing so.

With respect to curcumin hybrids, the other (non-curcumin) component is generally a beneficial molecule with desirable traits. For example, other hybrid components may be various antioxidants, various metal chelators, etc. Specific examples of such molecules include but are not limited to: melatonin.

Exemplary hybrid molecules that comprise curcumin include but are not limited to: curcumin-melatonin hybrids, etc. Curcumin hybrids are generally formed by combining two or more molecules comprising at least the essential (active) moieties of curcumin (e.g. having anti-AβO activity, and at least the essential portions of a second molecule of interest, e.g. a portion of the molecule that retains a desired activity. The step of combining takes place under conditions and in a manner that allows a chemical reaction to occur between the two hybrid components, and which allows attachment of the molecule of interest to curcumin at one or more reactive groups or positions of curcumin, e.g. one or more or the three OH groups of curcumin. However, this generally does not include attachment to carbon at the C3 position, since this position is typically used to attach the spacer molecule which connects the curcumin moiety to the CM/LR anchor, and hence is occupied.

Cell Membrane/Lipid Raft (CM/LR) Anchor

The bivalent ligands of the invention also include a cell membrane/lipid raft (CM/LR) anchor. This component is a moiety that is able to target, insert into, be incorporated, introduced or interposed into and/or otherwise efficiently interact with CM/LR. This moiety generally interacts with cell membranes and/or lipid rafts non-covalently, based on entropy driven hydrophobic interactions, although covalent and polar interactions are not excluded. Any moiety which can effectively be incorporated into LRs while still remaining attached to a spacer (that is also attached to a AβO-inhibitor/antioxidant agent), thereby juxtaposing or positioning the AβO-inhibitor/antioxidant agent in proximity to the LR, may be used in the practice of the invention. Such CM/LR anchors are generally hydrophobic, allowing them to be readily incorporated into membranes and lipid rafts, which contain a high proportion of hydrophobic lipids. The anchors generally have molecular weights in the range of from about 100 to about 1000, and usually from about 300 to about 500 Mr. Suitable CM/LR anchor moieties include but are not limited to: various polycyclic hydrocarbons examples, which include but are not limited to: steroids and sterols which comprise four cycloalkane rings that are joined to each other, for example: steroids and waxy steroids such as cholesterol and derivatives thereof, e.g. cholesterol, cholesterylamine, dihydrocholesterol, disogenin; cyclic terpenes such as lupenol; various sterols; various long chain fatty acids such as palmitic acid and steric acid; etc.

Spacer or Linker Moiety

The curcumin and CM/LR moieties of the bivalent ligands of the invention are joined, spanned and/or chemically linked via a stable spacer or linking molecule, which may also be referred to herein as a linker, spacer or linking moiety, portion, part, etc. Generally, the spacer is an elongated chain of atoms and/or groups of atoms, the total length of which is from about 5 to about 40 atoms, or from about 10 to about 30 atoms, or from about 15 to about 25 atoms, with a preferred length being about 21 atoms. The linker generally comprises, for example, covalently joined atoms selected from e.g. carbon, nitrogen, and oxygen atoms, many of which are part of larger units such as $CH_2$ groups, ring structures, carbonyl groups, amine groups, etc. The atoms in the chain are generally chemically bonded via single bonds, although double bonds may also be present. The linker molecules typically contain reactive groups at or near their terminal ends to provide an opportunity to react chemically with the two other components of the BMAOI. One end of the spacer is generally connected to (usually covalently bonded to) the AβO-inhibitor/antioxidant moiety of the BMAOI. For example, when the AβO-inhibitor/antioxidant moiety is curcumin, a covalent bond may be formed between the linker and the carbon at position C3 of the curcumin moiety. However, attachment to other positions of the curcumin moiety is also contemplated. The opposite end of the spacer is connected to the CM/LR anchor, usually via a covalent bond to a reactive group of that molecule, e.g. to a hydroxyl, amine, or other accessible reactive group.

Various Embodiments

In some embodiments, the AβO-inhibitor is curcumin or a curcumin-melatonin hybrid (FIG. 15), and the anchor to the CM/LR is cholesterol, cholesterylamine or diosgenin. The AβO-inhibitor and the CM/LR anchor are connected by a spacer or linker moiety as described herein.

Methods

The methods of the invention involve identifying subjects or patients who might benefit from receiving therapy such as administration of the one or more of the bivalent ligands described herein. Such subjects or patients are generally mammals, and usually humans, although this need not always be the case, since veterinary and research related applications of the technology are also contemplated. Generally a suitable subject or patient is identified by a health care professional or professionals using known tests, measurements or criteria for either already having symptoms of AD, or being at risk of developing symptoms of AD. A suitable treatment protocol is then developed. The methods may also comprise one or more steps related to monitoring the effects or outcome of administration in order to evaluate the treatment protocol and/or to adjust the protocol as required or in a manner that is likely to provide more benefit, e.g. by increasing or decreasing doses of medication, or by changing the particular type of mimic that is administered, or by changing the frequency of dosing or the route of administration, etc. While in some cases the improvement or lessening of symptoms (or the prevention of symptoms) that occurs may be complete, e.g. the functioning of the patient returns to or remains normal (as assessed in comparison to suitable control subjects or standardized values obtained therefrom), this need not always be the case. Those of skill in the art will recognize that even a lower level of improvement in symptoms may be highly beneficial to the patient, as may be the slowing of the progression of the disease, even if a complete cure does not result.

The methods of the invention involve administering compositions comprising at least one (i.e. one or more) of the BMAOIs disclosed herein (which may be referred to as bivalent ligands) to a patient in need thereof. The present invention thus also provides compositions which comprise the bivalent ligands as described herein, usually together with a pharmacologically suitable carrier or diluent. In some embodiments, one substantially purified bivalent ligand is present in a composition; in other embodiments more than one bivalent ligand is present, each bivalent ligand being substantially purified prior to being mixed in the composition. The preparation of pharmacologically suitable compositions for use as medicaments is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of bivalent ligand in the formulations may vary. However, in general, the amount in the formulations will be from about 1% to about 99%.

The bivalent ligand compositions (preparations) of the present invention may be administered by any of the many suitable means which are well known to those of skill in the art, including but not limited to: by injection, inhalation, orally, intravaginally, intranasally, by ingestion of a food or product containing the mimic, topically, as eye drops, via sprays, etc. In preferred embodiments, the mode of administration is orally or by injection. In addition, the compositions may be administered in conjunction with other treatment modalities such as other agents which are used to treat AD or the conditions which cause AD in the patient, examples of which include but are not limited to the administration of anti-depressants and psychoactive drugs, administration of dopamine and similar agents, administration of e.g. donepezil, galantiamine, memantine, tacrine, rivastigamine, etc.

The amount of BMAOI that is administered is generally in the range of from about 1 to about 20 mg/kg, and preferably in the range of from about 5 to about 10 mg/kg, although as one of skill in the art will recognize, the precise amount may vary depending on one or more attributes of the drug recipient, including but not limited to: weight, overall health, gender, age, nationality, genetic history, other conditions being treated, etc.

The bivalent ligands of the invention may be used to treat or prevent the symptoms that occur as a result of the formation of Aβ oligomers and/or aggregation of such oligomers in brain tissue. Any disease or condition that results from the abnormal production and/or accumulation of Aβ oligomers may be treated using the compounds of the invention. Such diseases or conditions and symptoms thereof are usually termed or associated with Alzheimer's disease (AD). In some embodiments the compounds described herein are used prophylactically, e.g. they are administered to persons who have not yet exhibited symptoms of the disease but are deemed to be at risk for developing the disease (e.g. those who are known to have a genetic predisposition for disease development), or simply those who are at risk due to other factors such as aging. The compounds may also be administered to individuals who are thought or deemed to be exhibiting early signs of disease or to be in early stages of disease. The compounds may also be administered to individuals who are known to have and who definitely exhibit symptoms of disease. Administration of the compounds described herein may prevent disease symptoms, may slow the progression of disease, and/or may actually reverse symptoms. Those of skill in the art will recognize that, while complete remission of disease may be desirable, great benefit may also accrue if partial remission or slowing of disease progress is achieved.

Diagnostic Imaging of β-Amyloid (Aβ) Plaques

The invention also provides methods of imaging or visualizing β-amyloid (Aβ) plaques in brain tissue for diagnostic purposes, e.g. to determine whether Aβ plaques are present in the brain of a subject who is either living or deceased. This is possible because generally one or more moieties of the compounds of the invention are fluorescent, especially curcumin, emitting detectable fluorescence when exposed to suitable light or other forms of electromagnetic energy. According to the method, brain tissues containing or suspected of containing Aβ plaques is exposed to at least one BMAOI as described herein, and then to a suitable excitatory wavelength of energy and the subsequent emission of energy from the compounds is detected. In some embodiments, the method may include a step of removing (e.g. washing) unbound BMAOI from the brain tissue prior to detection of fluorescence.

Exposure may be carried out either in vivo in a living patient or on post mortem samples. For in vivo applications, the method can be used to assist with the diagnosis of disease, and/or to monitor disease therapy. One advantage of the present invention is that administration of the compounds to treat AD provides a "built in" means to visualize the status of the disease in the patient. In this embodiment, one or more compounds of the invention is administered to a patient who might benefit from the method, and the insertion of the BMAOIs into CM/LRs within the patient's brain is then monitored using fluorescence monitoring techniques that are known in the art. Post-mortem and/or in vitro use of the compounds is also carried out by exposing brain tissue (either in situ or tissue from a brain biopsy) to at least one compound, and then visualizing fluorescence of the compounds incorporated into CM/LRs. Techniques for such visualization are known in the art, e.g. confocal microscopy, fluorescence microscopy, etc.

EXAMPLES

Example 1

"Clicked" Bivalent Ligands Containing Curcumin and Cholesterol as Multifunctional Aβ Oligomerization Inhibitors: Design, Synthesis, and Biological Characterization Abstract In our effort to develop multifunctional compounds that co-target beta-amyloid oligomers (AβOs), cell membrane/lipid rafts (CM/LR), and oxidative stress, a series of bivalent multifunctional Aβ oligomerization inhibitors (BMAOIs) containing cholesterol and curcumin were designed, synthesized, and biologically characterized as potential treatments for Alzheimer's disease (AD). The in vitro assay results established that the length of spacer that links cholesterol and curcumin and attaching position of spacer on curcumin are important structural determinants for their biological activities. Among the BMAOIs tested, 14 with a 21-atom-spacer was identified to localize to the CM/LR of human neuroblastoma MC65 cells, to inhibit the formation of AβOs in MC65 cells, to protect cells from AβOs-induced cytotoxicity, and to retain antioxidant properties of curcumin. Furthermore, 14 was confirmed to have the potential to cross blood-brain barrier (BBB) as demonstrated in Caco-2 cell model.

Introduction

The etiology of AD still remains elusive and multiple factors have been suggested to contribute to the development of AD, among which amyloid-β (Aβ) and oxidative stress have been well documented.[1,2] Recently emerging evidence indicate that small Aβ oligomers (AβOs), rather than insoluble Aβ fibrils, are responsible for disruption of neuronal synaptic plasticity and the resulting early cognitive impairment associated with AD.[3] Studies of brain samples from AD patients also confirmed the correlation of AβOs with the severity of demenfia.[4,5] Despite the fact that multiple assemblies of AβOs and a variety of underlying mechanisms have been suggested in the literature,[7-11] one point of consensus remains clear: the requirement of AβOs. Collectively, these findings provide compelling support for developing Aβ oligomerization inhibitors as novel therapeutic agents for the treatment of AD. Increased oxidative damage by reactive oxygen species (ROS) and reactive nitrogen species is another feature consistently found in the brains of AD patients.[2,12] Many factors have been demonstrated to cooperatively contribute to the production of ROS in the AD brain such as biometals, mitochondria dysfunction and Aβ.[13] Transgenic mouse studies have also showed a correlation of increased oxidative stress and Aβ accumulation.[14]

Recently a wealth of data has implicated the roles of neuronal cell membrane/lipid rafts (CM/LR) in the oligomerization and toxicity of Aβ.[15,16] Once associated with the membranes, Aβ exhibits an enhanced rate of aggregation that is dependent on pH, metal ion and ganglioside interactions.[17-19] Recently, evidence has also indicated that lipid rafts, a cell membrane microdomain enriched in cholesterol and sphingolipids, can accelerate the cell membrane binding of Aβ and AβOs formation.[15,16] On the other hand, destruction of lipid rafts affects Aβ membrane binding and protects cells from Aβ toxicity.[20] Furthermore, Aβ precursor protein (APP), APP cleavage enzymes (β- and γ-secretases), Aβ and AβOs have all been identified in lipid rafts, suggesting that lipid rafts may be a critical platform for Aβ to production and oligomerization.[21] In addition, oxidative stress has been shown to up-regulate presenilin-1, the critical component of γ-secretase, in lipid rafts of neuronal cells to promote Aβ production.[22] Altogether, it is apparent that CM/LR are important regulators in AD development and this relationship can be exploited to design and develop novel AD therapies.

Numerous chemical ligands have been developed as potential AD treatments by targeting Aβ and oxidative stress.[23,24] However, very few of them moved to clinical trials and none of them has been approved by FDA, which suggests that targeting a single risk factor is not an ideal strategy for developing treatments for this multifaceted disease. New approaches that co-target multiple risk factors involved in AD are emerging as promising strategies for developing effective treatment agents for AD.[25-27] Herein, we show that a bivalent multifunctional Ad oligomerization inhibitor (BMAOI) strategy that targets AâOs, oxidative stress and CM/LR is a novel approach to design strategically distinct ligands with the potential to overcome the limits posted by the traditional single-factor based approach. Conceptually, these BMAOIs contain a multifunctional AβO-inhibitor phannacophore that accommodates additional antioxidant properties as well as a CM/LR anchor pharmacophore linked by a spacer (FIG. 1). The use of bivalent strategies to explore protein-protein interactions has been particularly successful in the opioid receptor research field.[28] Recently, this concept has been extended to neurodegenerative diseases in developing acetylcholinesterase inhibitors and metal chelators.[25] We envisaged that such BMAOIs would chaperone the multifunctional AβO-inhibitor moiety in close proximity to CM/LR in which AβOs and oxidative stress are produced to increase its accessibility to interfere with these multiple processes, thus improving its clinical efficacy (FIG. 1). In this report, we describe the rational design, synthesis and biologically characterization of a series of BMAOIs.

Design and Chemistry.

Figure 2:
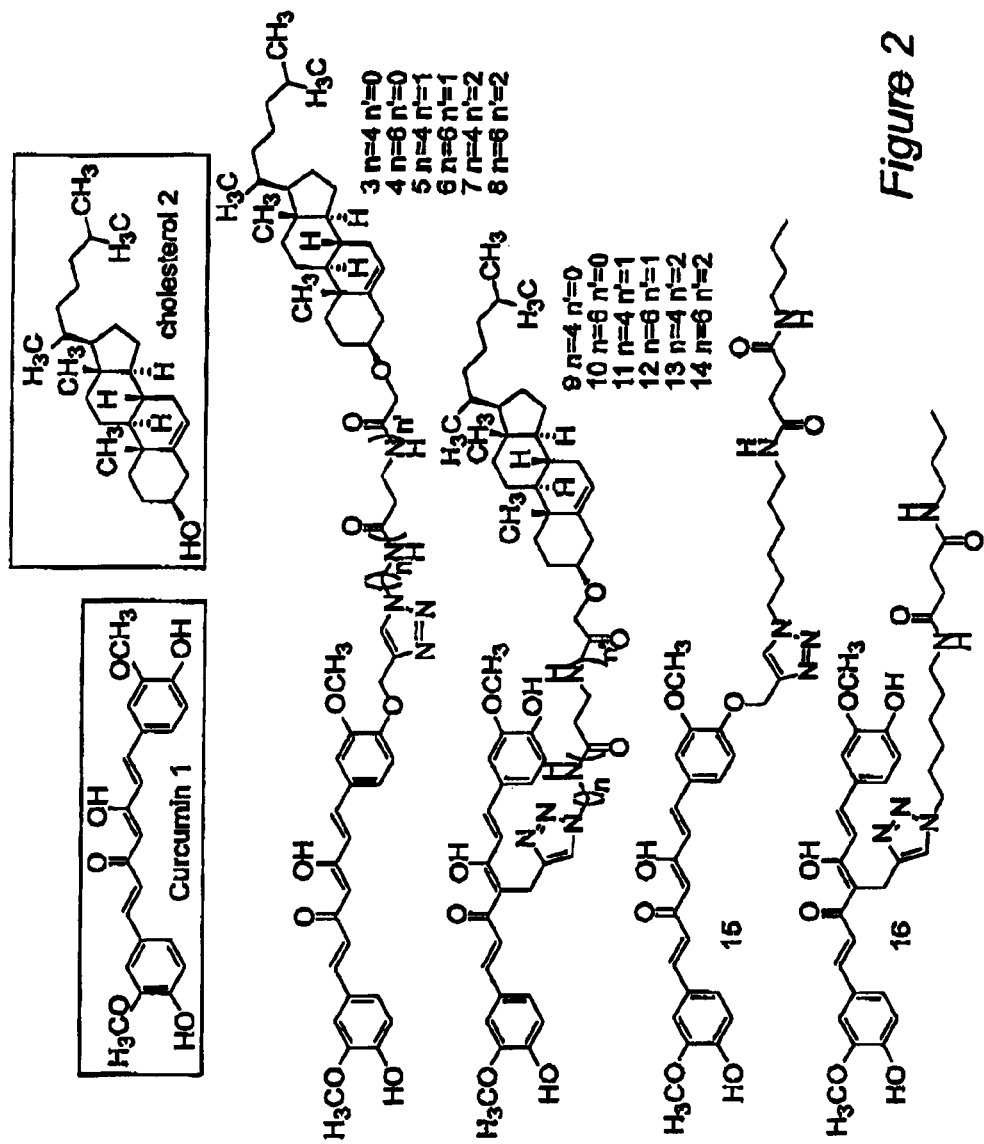
FIG. 2. Chemical structures of building blocks 1 (curcumin) and 2 (cholesterol) and several designed BMAOIs and monovalent ligands.

The desired BMAOIs must contain an AβO-inhibitor moiety with intrinsic antioxidant effects, as well as incorporate a residue able to efficiently interact with CM/LR, spanned by a stable linkage. Thus in our designed BMAOIs, curcumin (1) was selected as the multifunctional AβO-inhibitor pharmacophore and on the other end, connected by a spacer, cholesterol (2) was selected as the anchor pharmacophore to the CM/LR (FIG. 2). The selections of 1 and 2 were based on the following reasons: 1) 1 is an important phytochemical that has long been known for its antioxidant, anti-inflammatory properties as well as recently discovered anti-Aβ properties;[29-32] 2) it has been demonstrated that 2 and other sterols linked with another moiety can anchor CM/LR in mammalian cells and function as a carrier to induce internalization via endocytosis.[33,34] The crucial consideration in designing BMAOIs is to determine the loci on the two pharmacophores for attaching the spacer and the nature and length of the spacer. Given the fact that alkylation of the 3-OH of 2/sterol does not affect their binding affinities to CM/LR,[33,34] we selected this position as spacer attachment position. On the other end, one of the phenolic oxygens and the C-4 position (methylene carbon between the two carbonyl groups) of 1 were selected to design two series of BMAOIs to investigate the optimal attachment. Since it is not clear whether Aβ oligomerization occurs on the surface or inside of CM/LR and optimal spacer length range cannot be predicted from existing literature, we varied spacer length as a key parameter for investigation. Since the cell membrane thickness is frequently cited as 3 nm (although ranging from 2.5 to 10 nm), we decided to initially vary the spacer length from 11 to 21 atoms (FIG. 2). Two monovalent ligands (1 attached to spacer but not cholesterol) (15 and 16) were also designed to evaluate the influence of spacer attachment on 1's activity. Recently "click chemistry"[35] methodology has been successfully applied to connect 1 to peptides by Ouberai et al.[36] Therefore, to efficiently assemble the two phaunacophores together, we adopted this "click chemistry" methodology to include a 1,4-disubstituted triazole ring in the spacer.

The synthesis began with the preparation of alkyne intermediates 20 and 23 through well established Pabon reaction (Scheme 1).[37] Briefly, alkylation of vanillin 17 with propargyl bromide provided 18. Aldol reaction of 17 with 2,4-pentane-dione followed by another Aldol reaction with 18 afforded intermediate 20. Alkylation of 2,4-pentane-dione with propargyl bromide in the presence of 1,8-Diazabicycloundec-7-ene (DBU) in benzene yielded 22 which on Aldol reaction with 17 afforded intermediate 23.

Scheme 1. Synthesis of intermediates 20 and 23.

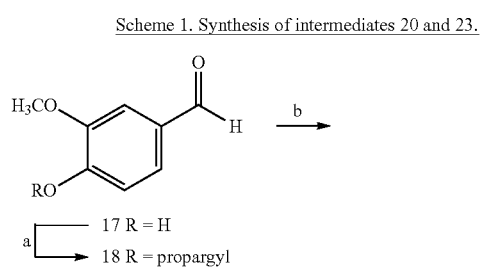

17 R = H
18 R = propargyl a) Propargyl bromide

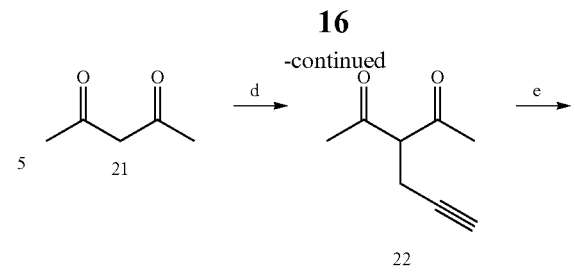

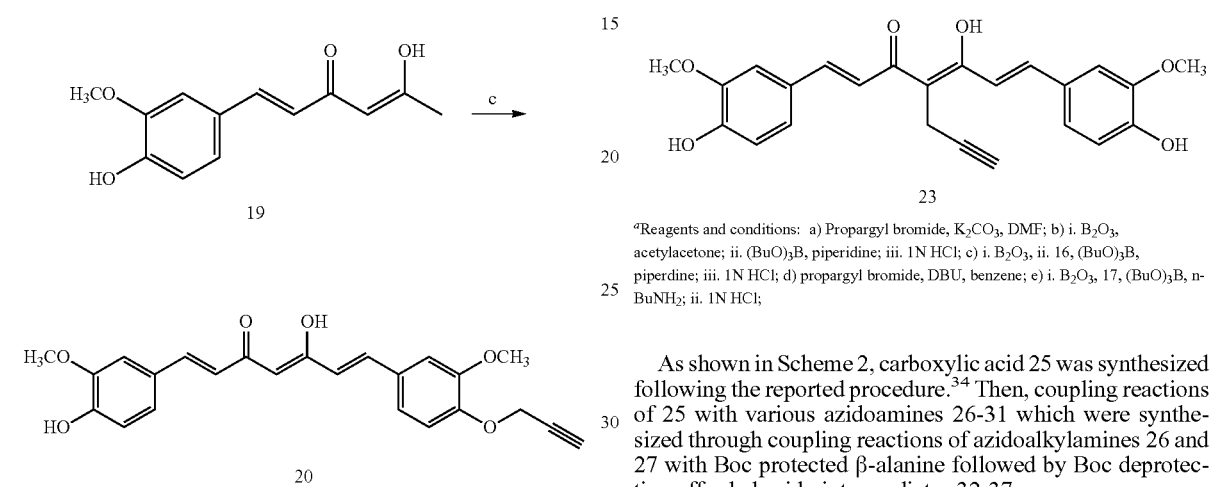

*Reagents and conditions: a) Propargyl bromide, $K_2CO_3$, DMF; b) i. $B_2O_3$, acetylacetone; ii. $(BuO)_3B$, piperidine; iii. 1N HCl; c) i. $B_2O_3$, ii. 16, $(BuO)_3B$, piperdine; iii. 1N HCl; d) propargyl bromide, DBU, benzene; e) i. $B_2O_3$, 17, $(BuO)_3B$, n-BuNH$_2$; ii. 1N HCl;

As shown in Scheme 2, carboxylic acid 25 was synthesized following the reported procedure.[34] Then, coupling reactions of 25 with various azidoamines 26-31 which were synthesized through coupling reactions of azidoalkylamines 26 and 27 with Boc protected β-alanine followed by Boc deprotection afforded azido intermediates 32-37.

Scheme 2. Synthesis of intermediates 32-37.

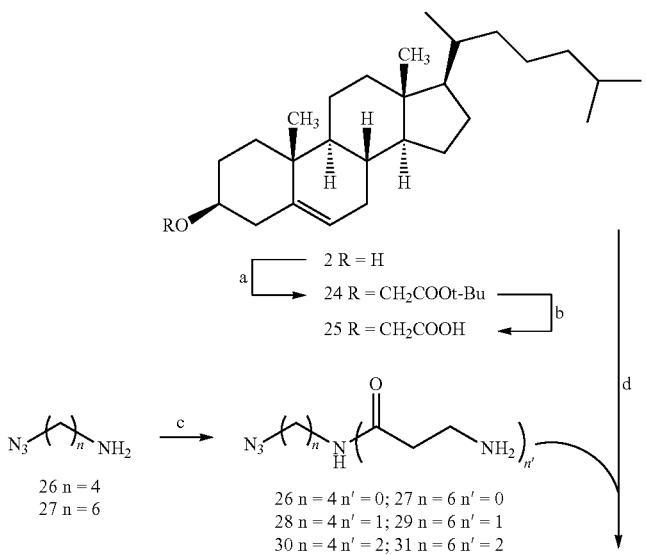

2 R = H
24 R = $CH_2COOt$-Bu
25 R = $CH_2COOH$ 26 n = 4
27 n = 6

26 n = 4 n' = 0; 27 n = 6 n' = 0
28 n = 4 n' = 1; 29 n = 6 n' = 1
30 n = 4 n' = 2; 31 n = 6 n' = 2

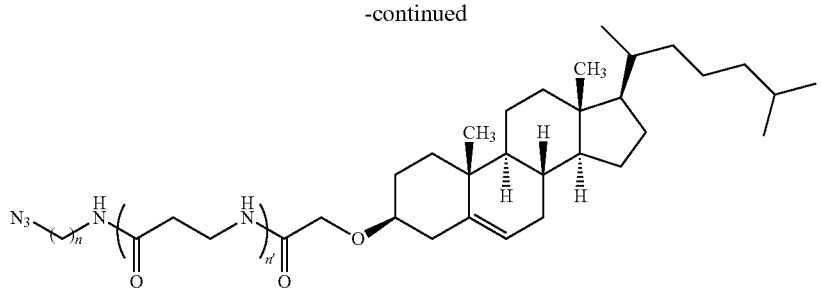

32 n = 4 n' = 0; 33 n = 6 n' = 0
34 n = 4 n' = 1; 35 n = 6 n' = 1
36 n = 4 n' = 2; 37 n = 6 n' = 2

[a]Reagents and conditions: a) tert-butyl-2-bromoacetate, NaH, THF; b) formic acid/Et$_2$O; c) i. Boc protected beta-alanine or Boc protected beta-alanylalanine, EDC, HOBt, CH$_2$Cl$_2$; ii. TFA/CH$_2$Cl$_2$; d) EDC, HOBt, CH$_2$Cl$_2$.

Once all the required intermediates were available, the click reactions of the alkynes 20 or 23 with 32-37 were applied under sodium ascorbate and CuSO$_4$ in THF/H$_2$O conditions to obtain the designed BMAOIs 3-8 or 9-14, respectively (Scheme 3). All the designed BMAOIs are in keto-enol forms in chloroform judged by $^1$HNMR and $^{13}$CNMR. The synthesis of the monovalent compounds 15 or 16 is similar to the synthesis of BMAOIs. Click reactions of 20 or 23 with azido intermediate 38 which was synthesized from the reaction of butylamine with succinic anhydride followed by amide coupling with 6-azidohexylamine achieved the synthesis of 15 or 16, respectively.

Scheme 3. Synthesis of designed BMAOIS and monovalent ligands.

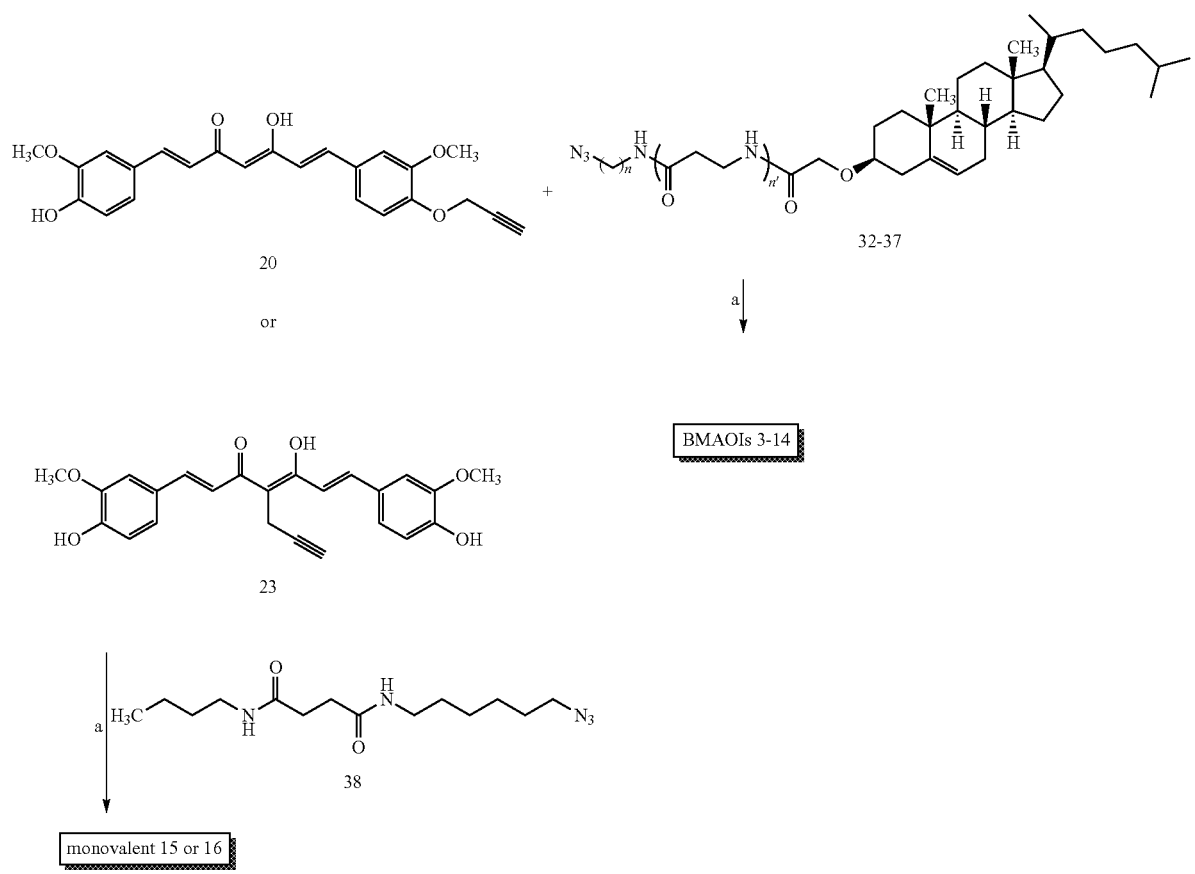

[a]Reagents and conditions: a) CuSO$_4$, sodium ascorbate, THF/H$_2$O (1:1).

Results and Discussion

Figure 3A:
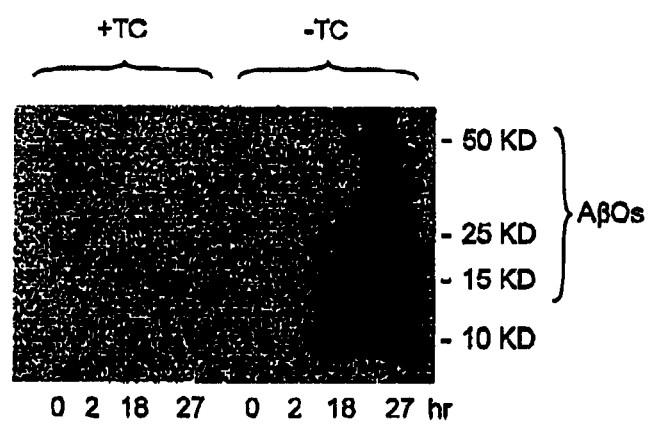
FIG. 3A-C. Inhibition of AβOs formation by 14 in MC65 cells and ML60 cells. A. MC65 cells were cultured with and without tetracycline (TC) i.e. under +TC or −TC conditions for varying intervals (0, 2, 18, 27 hrs), then cell lysates were analyzed by Western blot using 6E10 antibody. B. MC65 cells were treated with indicated compounds (10 μM) for 24 hrs immediately after the removal of TC. Lysates from cultures were analyzed by Western blotting using 6E10 antibody. The image represents the results from one of three independent experiments. C. ML60 cells were treated with test compounds (10 μM) for 24 hrs and extracellular AβOs in condion IL-2 augmented NK cell activity in vitro. The experiments were performed as described in the Experimental section. Data were presented as mean (n=4)±SEM. *P<0.05 indicates significant differences from control group (without TC in A and without AβOs in B) analyzed by one-way ANOVA.
Figure 3B:
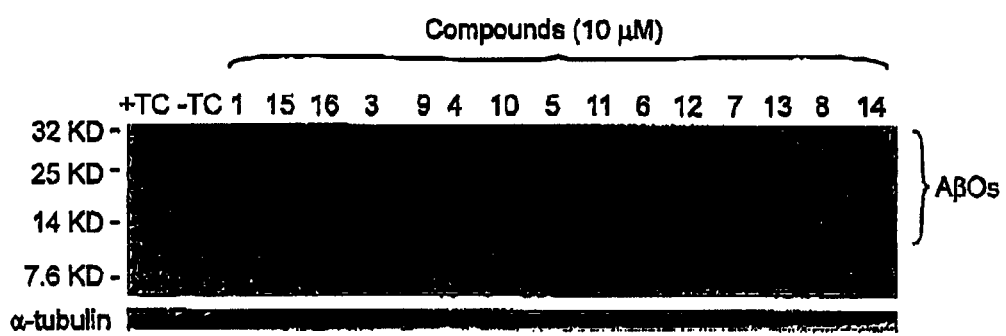
Figure 3C:
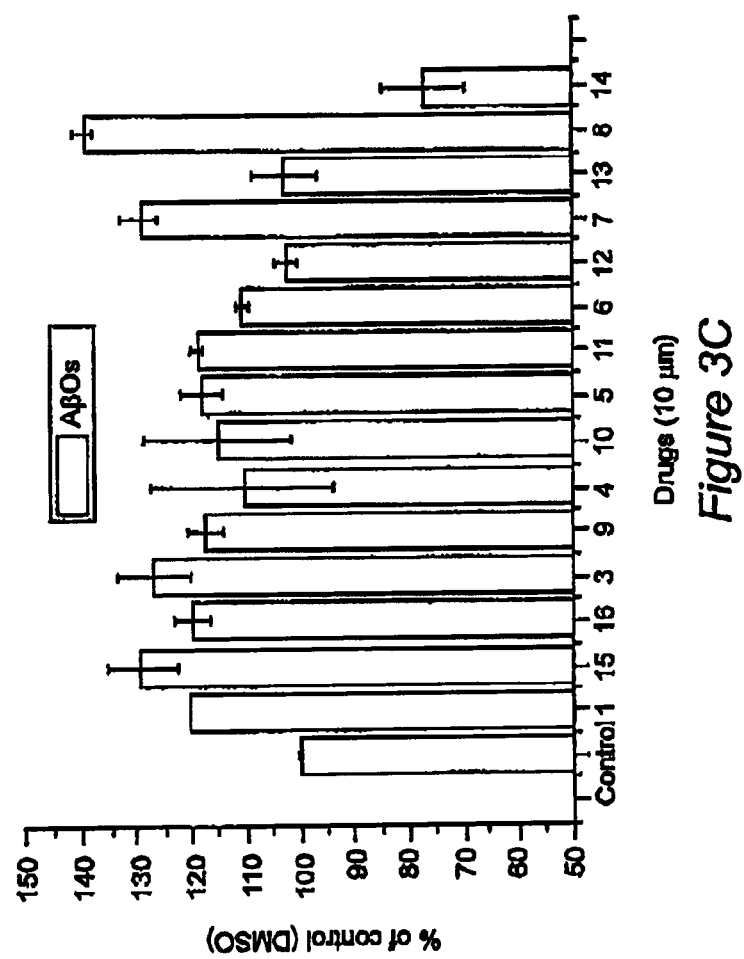

Inhibition of AβOs production by designed BMAOIs. The rational design of BMAOIs targeting CM/LR and AβOs as well as oxidative stress will require demonstration of anticipated effects in a biologically relevant system. The whole cell assay is a composite of not only Aβ oligomerization inhibition but also permeability, stability and other factors will validate the accessibility and function of our BMAOIs. MC65 is a human neuroblastoma cell line that conditionally expresses C99, the C-terminus fragment of APP using tetracycline (TC) as transgene suppressor.[38] Upon removal of TC, these cells can produce intracellular Aβ aggregates including small AβOs. Most importantly, the induced cytotoxicity in these cells by TC removal has been associated with the accumulation of AβOs.[39] Furthermore, oxidative stress has been indicated as one potential effector to impart neurotoxicity upon the accumulation of intracellular AβOs in these cells.[40] Therefore, MC65 cells were initially employed to validate and test our BMAOIs using Western blot analysis. All BMAOIs were first evaluated at a single concentration of 10 μM. Candidate compounds with inhibitory activities at this concentration were further evaluated in a dose-dependent manner in the following assays. As shown in FIG. 3A, withdrawal of TC induced the production of AβOs consistent with reported results.[39] 1 did not exhibit inhibition on the formation of AβOs (FIG. 3B). Spacer attachment at both positions (15 and 16) did not change the activity of 1. BMAOIs 3, 4 and 9, 10 (spacer length ranging from 11 to 13 atoms) showed no inhibition on the formation of small AβOs. BMAOIs 5-7 and 11-13 (spacer length ranging from 15 to 19 atoms) slightly inhibited the formation of AβOs with specific suppression of the 24-kD bands. Notably, among the BMAOIs tested, 14 (with 21 atoms in the spacer) significantly inhibited AβOs production. This may indicate that spacer length is an important structural determinant for their inhibition on AβOs formation in MC65 cells with a 21-atom-spacer best supporting the design of BMAOIs tested here. Most importantly, it is notable that 8, with the same spacer length (21 atoms) as 14 but different spacer attaching position on 1, did not show inhibitory effects on AβOs formation, which suggests the importance of attachment position on 1 as well. Next, another cell line, ML60, was employed to evaluate the inhibition of AβOs production. ML60 cell line is a line of Chinese hamster ovary (CHO) cells stably expressing wild type APP and mutant presenilin I (M146L missense mutation) and can specifically produce high levels of extracellular AβOs.[41] As shown in FIG. 3C, only 14 inhibited the production of extracellular AβOs in ML60 cells and surprisingly all the other compounds increased the production of AβOs at tested concentration (10 μM). It has been demonstrated that AβOs are formed intracellularly and then excreted outside the cells.[42] The results from ML60 cells may further reflect 14's ability to reduce intracellular AβOs, which is consistent with the results from MC65 cells. Altogether, these results suggest that spacer length and attachment position on 1 are important structural determinants for inhibitory activities on the formation of AβOs and BMAOIs with optimal spacer length can improve their potencies.

In order to further confirm the inhibition of small AβOs by 14 in MC65 cells, an AβO-specific antibody A11[43] combined with Alexa Fluor 568 conjugated secondary antibodies was employed to detect the expression of AβOs in MC65 cells using immunocytochemistry techniques. The immunocytochemistry: comparison of 1 (curcumin) and compound 14 was carried out in MC65 cells. MC65 cells were treated with the indicated compounds (10 μM) immediately after the removal of TC. After 24 hrs, the cells were fixed and immunofluorescently stained for AβOs, CM/LR, and nucleus and imaged with a Leica TCS-SP2 AOBS confocal laser scanning microscope. Five areas were examined. The results (not shown) indicated that removal of TC induced rapid intracellular accumulation of AβOs. Consistent with Western blot results, 14 significantly inhibited the formation of AβOs in MC65 cells upon the removal of TC. Surprisingly, 1 (curcumin) slightly suppressed the formation of AβOs in this assay while it exhibited no inhibitory effects on the formation of AβOs in Western blot analysis. This might be due to the different antibodies used for detection in these two assays with A11 antibody more specific to AβOs. In addition to confirming Western blot data, these results also indicate that both 14 and 1 can cross the cell membrane of MC65 cells.

Interactions of 14 with AβOs and cell membrane of MC65 cells. In order to confirm 14 can bind to AβOs, the inhibition of Aβ42 oligomerization was performed and assessed using Western blot analysis as described in literature[29] in order to investigate binding interactions of 14 with Aβ42 and the CM/LR of MC65 cells. Briefly, Aβ42 (5 μM) was incubated with or without compounds (20 μM), then samples were analyzed by Western blot using 6E10 antibody. MC65 cells were treated and imaged as described in the previous paragraph. Differential Interference Contrast (DIC) images of the MC65 cells were obtained.

The results showed that Aβ42 formed oligomers under the reported protocol as demonstrated by transmission electron microscope (TEM) analysis (not shown). After incubation in Ham's F-12 medium for 4 hr at 37° C., higher order species of AβOs were formed. Notably, both 1 and 14 inhibited the oligomerization of Aβ42, which demonstrates their direct binding to Aβ42. This further confirms that the addition of a spacer in 14 does not affect its binding interactions with Aβ42. Next, immunocytochemistry studies were conducted to confirm the interactions of 14 with the CM/LR taking advantage of the intrinsic fluorescence of 14. The results showed that 14 was detected primarily on the cell membrane of MC65 cells but also inside of MC65 cells as well. In contrast, 1 was detected inside of MC65 cells but not on the cell membrane. The results demonstrated that 14 can directly interact with CM/LR of MC65 cells and anchor the ligand primarily to the CM/LR. Given the fact that Aβ aggregates on the cell surface,[17-19] the anchorage of 14 to CM/LR may increase its target accessibility and consequently increase its potency. Collectively, these results support our design rationale of using BMAOIs to co-target AβOs and CM/LR.

Figure 4A:
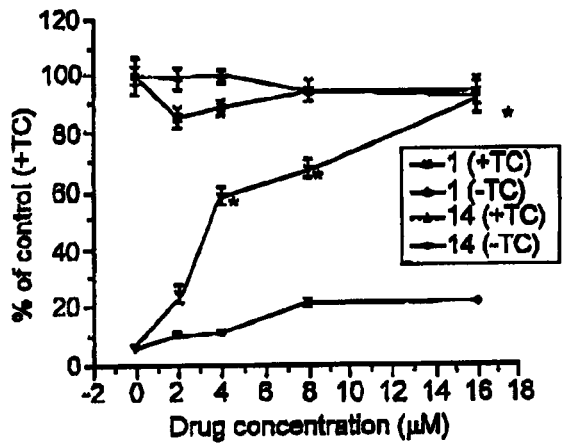
Figure 4C:
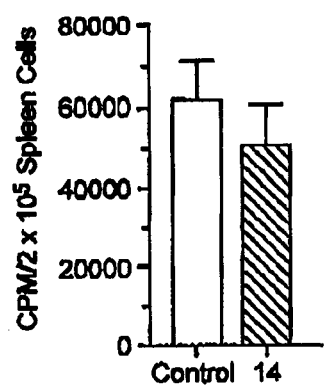
Figure 4B:
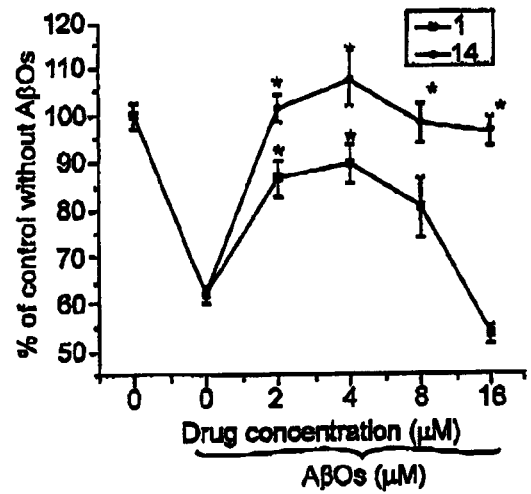
Figure 4D:
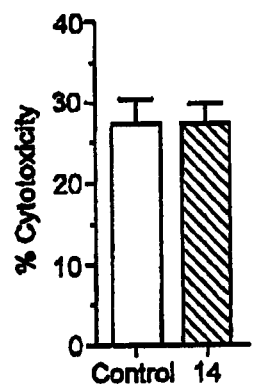

Protective effects of 14 on AβOs-induced cytotoxicity in MC65 cells and differentiated human neuroblastoma SH-SY5Y cells. The production of intracellular AβOs has been suggested to be the major factor leading to cytotoxicity in MC65 cells.[39] Therefore, to test whether the suppression of AβOs formation by 14 correlate with functional activities, 14 was further evaluated for its protective effects on MC65 cell viability upon removal of TC. As shown in FIG. 4A, 1 and 14 exhibited no toxic effects at tested concentrations in the presence of TC. Upon removal of TC, MC65 cell viability was significantly decreased and 14 protected MC65 cell survival in a dose-dependent manner with nearly full rescue at 16 μM. 1 only exhibited minimal protective effects on MC65 cell viability consistent with reported results.[39] 8 and 12 exhibited no protective effects under these conditions (data not shown) which further suggests the importance of spacer length and attachment position on their activities. Together with the results from Western blot and immunocytochemistry assays, these data suggest that the localization of 14 to the CM/LR may increase 14's target accessibility and produce a more profound inhibition of the formation of AβOs and elevate the survival of MC65 cells. To further verify whether 14 can protect cells from extracellular AβOs-induced cytotoxicity, all trans-retinoic acid differentiated human SH-SY5Y cells were employed. As shown in FIG. 4B, freshly prepared AβOs (1 μM) from Aβ42 significantly decreased SH-SY5Y cell viability (~40% decrease). Notably, 14 completely restored the cell viability at all of the tested concentrations. On the other hand, 1 only exhibited moderate protective activities at 2, 4, and 8 μM concentrations but not at 16 μM. This may be due to its toxic effect on SH-SY5Y cells at this concentration since 1 has been reported to have cytotoxicity on SH-SY5Y cells at higher concentrations.[44] These results suggest that 14 can protect cells from both intracellular and extracellular AβOs-induced cytotoxicity, while 1 only exhibits protective activity towards extracellular AβOs-induced cytotoxicity even though it can cross the cell membrane under these experimental conditions. This may further indicate that while both 1 and 14 can bind to AβOs, CM/LR anchorage of 14 can increase its accessibility to intracellular target AβOs. Since CM/LR are crucial for many aspects of cell signaling and functions, 14 was further evaluated for its potential cytotoxicity in mouse spleen and natural killer (NK) cells. 14 showed minimal cytotoxic effects in mouse spleen (FIG. 4C) and no cytotoxic effects in NK cells (FIG. 4D). This suggests that localization of BMAOIs to the CM/LR will not affect normal cellular functions. Taken together, it is clear that 14 is more active than 1 in inhibiting the production of AβOs and in protecting cells from the in situ AβOs-induced cytotoxicity.

Antioxidant activity of 14. One of the BMAOIs design goals is to reduce oxidative stress that potentially contributes to the development of AD. Furtheuuore, oxidative stress has been indicated as one potential effector to impart neurotoxicity upon the accumulation of intracellular AβOs in MC65 cells.[40] Therefore, we decided to further evaluate the antioxidant activity of 14 in MC65 cells. Despite the availability of several chemical antioxidation assays, the ability to predict and correlate these chemical assays with in vivo activity is questionable. In contrast, a cellular antioxidation assay may provide a more biologically relevant system that best addresses the permeability, distribution, and metabolism issues to evaluate potential antioxidant properties. Recently, a dichlorofluorescein diacetate (DCFH-DA) based cellular antioxidant assay has been established and widely used for this purpose.[45] We therefore adopted this DCFH-DA assay in MC65 cells to evaluate the antioxidant effects of 14 and 1. As shown in FIG. 5A, upon TC removal, intracellular oxidative stress, as measured by fluorescence intensity, is significantly increased compared to normal growing MC65 cells in the presence of TC. Notably, both 14 and 1 suppressed the intracellular oxidative stress in a dose-depndent manner. These results may indicate that the curcumin moiety in 14 is responsible for its antioxidant activities. Although 1 exhibited antioxidant activities in this cellular model, it did not protect MC65 cell survival (FIG. 4A). To compare whether other antioxidants can protect MC65 cells from AβOs-induced cytotoxicity, N-acetylcysteine (NAC) and trolox (6-hydroxy-2,5,7,8-tetramethyl chroman-2-carboxylic acid), an analog of vitamin E, were tested in MC65 cells. As shown in FIG. 5B, trolox (32 μM) completely rescued MC65 cells from AβOs-induced cytotoxicity while NAC (8 mM) rescued MC65 cells by 48% consistent with reported results.[40] Given the fact that NAC is mainly a hydrogen peroxide scavenger while trolox, a chain-breaking antioxidant, is particularly effective against lipid peroxidation within the cell membrane,[46] these results may indicate lipid peroxidation within the cell membrane as a major contributor underlying the mechanism of AβOs-induced cytotoxicity in MC65 cells, which is consistent with the results from Woltjer et al.[47] The discrepancy of 1 and the other two antioxidants in MC65 cell-protection may suggest that 1 either cannot reach the targets or only partially suppress lipid peroxidation in MC65 cells. Together with the results from Western blot analysis, immunocytochemistry and cell protection, the results of antioxidation assay further suggest that 14 can retain the antioxidant property of 1 while exhibiting superior capability to reach intracellular AβOs by interacting with the CM/LR, thus efficiently reducing the formation of AβOs and ultimately exhibiting better overall protective activities in these cells when compared to 1. This further supports the idea that our BMAOIs strategy has the potential to provide clinically efficient multifunctional agents for treatment of AD.

Assessment of permeability and P-glycoprotein using Caco-2 cell model. Due to the adverse effects of AD in the central nervous system, effective drug candidates need to cross the blood-brian barrier (BBB). To test whether 14 has the potential to reach the brain, we determined its permeability and transport directionality using the Caco-2 model.[48] Although the Caco-2 cell monolayer model is derived from the colon rather than the brain, this model expresses efflux transporters such as P-glycoprotein which are also expressed at the BBB. The Caco-2 model does not predict BBB penetration as well as other models, such as PAMPA-BLM, ECV/C6, or hCMEC/D3[49-51], however, this model can provide early screening regarding the transcellular diffusional permeability and directional efflux transport across the BBB.[52] As shown in FIG. 5C, the apical-to-basolateral and basolateral-to-apical permeabilities of 14 were $7.1 \pm 4.6 \times 10^{-6}$ and $4.7 \pm 0.5 \times 10^{-6}$ cm/sec, respectively. Thus 14 exhibits good bi-directional permeability in Caco-2 cells. In contrast, we were unable to detect transport of 1, likely due to its extensive metabolism by glutathione-S-transferase enzymes.[53] This further indicates that CM/LR anchorage of 14 can improve its metabolic stability compared to 1. The peuneability directional ratio (efflux ratio) for 14 is 0.63, so it does not appear to be a substrate for BBB efflux transporters such as P-glycoprotein, since the efflux ratio is <2.[54] These data further support the potential of 14 as a new lead to develop effective AD treatment agents. Furthermore, in vivo studies have demonstrated the ability of 1 to cross the BBB,[29,55,56] so 14 is anticipated to be able to cross the BBB and the results from Caco-2 assay also supports this notion.

Conclusion

In summary, a series of BMAOIs containing 1 and 2 were designed and synthesized to co-target AβOs, oxidative stress, and CM/LR. Biological characterization from in vitro assays established that spacer length and the spacer attachment position on 1 are important structural determinants for their biological activities. Among the designed BMAOIs, 14 with a 21-atom-spacer was identified to localize to the CM/LR of MC65 cells, to efficiently inhibit the production of intracellular AβOs in MC65 cells, and to protect MC65 cells and differentiated SH-SY5Y cells from the cytotoxicity of AβOs. Furthermore, 14 exhibited antioxidant properties and demonstrated potential to cross the BBB using a Caco-2 model. These results strongly encourage further optimization of 14 as a new hit to develop more potent BMAOIs. These results may also help validate BMAOIs strategy as a novel design strategy to provide effective multifunctional ligands as potential AD treatment agents.

Experimental Section

Chemistry. Reagents and solvents were obtained from commercial suppliers and used as received unless otherwise indicated. All reactions were carried out under inert atmosphere ($N_2$) unless otherwise noted. Reactions were monitored by thin-layer chromatography (TLC) (precoated silica gel 60 $F_{254}$ plates, EMD Chemicals) and visualized with UV light or by treatment with Phosphomolybdic acid (PMA). Flash chromatography was performed on silica gel (200-300 mesh, Fisher Scientific) using solvents as indicated. $^1$HNMR and $^{13}$CNMR spectra were routinely recorded on Bruker ARX 400 spectrometer. The NMR solvent used was $CDCl_3$ or DMSO-d6 as indicated. Tetramethylsilane (TMS) was used as internal standard. The purity of target BMAOIs was determined by HPLC using Varian 100-5 C18 250×4.6 mm column with UV detection (288 nm) (40% acetonitrile/60% methanol/0.1% trifluoroacetic acid (TFA) and 38% acetonitrile/62% $H_2O$/2% acetic acid, pH 3.0 two solvent systems) to be ≥95%.

4-Methoxy-3-propargyloxy-benzaldehyde (18). A mixture of vanillin 17 (0.76 g, 4.90 mmol), $K_2CO_3$ (1.37 g, 9.90 mmol) and propargyl bromide (1.19 g, 6.90 mmol) in DMF (30 mL) was refluxed at 80° C. for 1 hr. Reaction mixture was cooled to 0° C. in ice bath and filtered through a short bed of celite. Ethyl acetate (50 mL) was added and the mixture was washed with 1N HCl (20 mL), extracted with ethyl acetate (100 mL). The organic phase was combined and washed with brine and dried over anhydrous $Na_2SO_4$. After filtration, solvent was removed under reduced pressure and the crude residue was purified by flash chromatography (hexane/ethyl acetate: 8/2) to afford 18 as white solid (0.74 g, 80%). $^1$HNMR (400 MHz, $CDCl_3$) δ 2.57 (t, 1H), 3.94 (s, 3H), 4.85-4.86 (d, J=2.44 Hz, 2H), 7.13-7.15 (d, J=8.16 Hz, 1H), 7.43-7.47 (m, 2H), 9.87 (s, 1H); $^{13}$CNMR (100 MHz, $CDCl_3$) δ 56.06, 56.65, 109.58, 112.71, 126.21, 131.00, 150.11, 152.17, 190.85.

5-hydroxy-1-(4-hydroxy-3-methoxy-phenyl)-7-(3-methoxy-4-propargyloxy-phenyl)-hepta-1,4,6-trien-3-one (20). Compound 20 was prepared by Pabon reaction following the reported procedure[57] from 2,4-pentane-dione and 17. $^1$HNMR (400 MHz, $CDCl_3$) δ 2.53-2.54 (t, J=4.84, 3H), 3.92-3.93 (d, J=6.2 Hz, 6H), 4.79-4.80 (d, J=2.32 Hz, 2H), 5.81 (s, 1H), 6.45-6.51 (m, 2H), 6.91-6.93 (d, J=8.2 Hz, 1H), 7.04 (s, 2H), 7.08-7.12 (m, 3H), 7.57-7.61 (d, J=15.72 Hz, 2H); $^{13}$CNMR (100 MHz, $CDCl_3$) δ 26.78, 55.97, 56.67, 60.41, 101.28, 109.70-129.31, 140.08-149.83, 182.83, 183.68.

3-propargyl-pentane-2,4-dione (22). The mixture of propargyl bromide (0.32 g, 2.70 mmol), $K_2CO_3$ (2.22 g, 16.10 mmol), and 2,4-pentane-dione (1.34 g, 13.40 mmol) in acetone (30 mL) was stirred for 24 hrs at 60° C. After filtration and removal of solvent under reduced pressure, the crude residue was purified by flash chromatography (hexane) to give 22 as colorless liquid (0.30 g, 69%). $^1$HNMR (400 MHz, $CDCl_3$) δ 2.03-2.04 (t, J=5.28 Hz, 1H), 2.22 (s, 3H), 2.25 (s, 3H), 2.68-2.71 (m, 2H), 3.84-3.87 (t, J=15.08 Hz, 1H); $^{13}$CNMR (100 MHz, $CDCl_3$) δ 14.45, 29.33, 29.41, 68.70, 70.79, 86.13, 202.18, 202.63.

1,7-Bis-(4-hydroxy-3-methoxy-phenyl)-4-propargyl-hepta-1,6-diene-3,5-dione (23). Compound 22 (0.81 g, 5.90 mmol) was reacted with boric anhydride (0.29 g, 4.10 mmol), 17 (0.18 g, 11.70 mmol), tributylborate (5.39 g, 23.40 mmol), and n-Butylamine (0.64 g, 8.80 mmol) following reported procedure[57] to afford 23 as yellow solid (0.50 g, 21%). $^1$HNMR (400 MHz, $CDCl_3$) δ 2.14-2.16 (t, J=5.08 Hz, 1H), 2.89-2.92 (m, 2H), 3.91 (s, 3H), 3.95 (s, 3H), 6.68-6.72 (d, J=15.8 Hz, 1H), 6.90-7.26 (m, 8H), 7.56-7.74 (m, 2H); $^{13}$CNMR (100 MHz, $CDCl_3$) δ 16.27, 56.03, 69.61, 70.57, 82.66, 106.24, 109.83-127.97, 142.43-148.87, 182.68, 193.34.

Cholesteryl-3-acetic acid (25). 25 was prepared following the reported procedure[33] from cholesterol as a white solid. $^1$HNMR (400 MHz, $CDCl_3$) δ 0.67 (s, 3H), 0.85-0.87 (dd, J=6.64 Hz, 1.68 Hz, 6H), 0.90-0.92 (d, J=6.52 Hz, 3H), 1.00-2.40 (31H), 3.26-3.34 (m, 1H), 4.14 (s, 2H), 5.36-5.37 (t, J=5.2 Hz, 1H); $^{13}$CNMR (100 MHz, $CDCl_3$) δ 11.86-42.33, 50.13, 56.17, 56.74, 65.20, 80.45, 122.40, 139.98, 173.89.

Procedure A. Preparation of 3-amino-N-(4-azido-butyl)-propionamide (28). To a mixture of Boc-protected β-alanine (1.00 mmol) and hydroxybenzotriazole (HOBt) (1.50 mmol) in $CH_2Cl_2$ (10 mL) was added 1-ethyl-3-(3-dimethylamino-propyl)-carbodiimide (EDC) (1.50 mmol) at 0° C. The reaction mixture was stirred for 1 hr at room temperature. Then, a solution of TFA salt of 4-azido-butylamine 26 (2.00 mmol) and $Et_3N$ (3.00 mmol) in $CH_2Cl_2$ (5 mL) was added to the reaction mixture at 0° C. The reaction mixture was then stirred overnight at room temperature. The reaction mixture was washed with $H_2O$, $NaHCO_3$, and brine. The organic phase was dried over anhydrous $Na_2SO_4$ and the solvent was removed under reduced pressure. The crude residue was purified by flash chromatography (MeOH/$CH_2Cl_2$: 3/97) and de-protected using TFA/$CH_2Cl_2$ (0.5 mL per 1 mmol of Boc-protected azido product) to afford 28 as a colorless viscous liquid. $^1$HNMR (400 MHz, DMSO-d6) δ 1.41-1.61 (m, 4H), 2.50-2.51 (m, 2H), 2.89-2.98 (m, 2H), 3.01-3.09 (m, 2H), 3.31-3.34 (t, J=13.32, 2H); $^{13}$CNMR (100 MHz, DMSO-d6) δ 25.74, 26.19, 32.01, 35.22, 37.90, 48.51, 50.33, 169.16.

3-amino-N-(6-azido-hexyl)-propionamide (29). 6-Azido-hexylamine 27 (2.00 mmol) was reacted with Boc-protected β-alanine (1.00 mmol) following Procedure A to give 29. $^1$HNMR (400 MHz, DMSO-d6) δ 1.20-1.46 (m, 8H), 2.40-2.44 (m, 2H), 2.84-2.87 (m, 2H), 2.93-2.98 (m, 2H), 3.21-3.24 (t, J=13.64, 2H); $^{13}$CNMR (100 MHz, DMSO-d6) δ 25.80, 25.89, 28.12, 28.78, 31.98, 35.25, 38.37, 50.55, 169.07.

3-Amino-N-[2-(4-azido-butylcarbamoyl)-ethyl]-propionamide (30). Compound 28 (2.00 mmol) was reacted with Boc-protected β-alanine (1.00 mmol) following Procedure A to give 30. $^1$HNMR (400 MHz, DMSO-d6) δ1.42-1.54 (m, 4H), 2.24-2.28 (t, J=14.2 Hz, 2H), 2.45-2.50 (m, 4H), 2.9-3.03 (m, 5H), 3.21-3.32 (m, 4H); $^{13}$CNMR (100 MHz, DMSO-d6) δ 25.71, 26.18, 26.25, 31.19, 32.03, 34.53, 35.19, 35.23, 35.39, 37.81, 38.83, 50.33, 51.69, 54.88,169.22, 170.15.

3-Amino-N-[2-(6-azido-hexylcarbamoyl)-ethyl]-propionamide (31). Compound 29 (2.00 mmol) was reacted with Boc-protected β-alanine (1.00 mmol) following Procedure A to give 31. $^1$HNMR (400 MHz, DMSO-d6) δ 1.22-1.54 (m, 10H), 2.22-2.25 (t, J=14.12 Hz, 2H), 2.9-3.1 (m, 6H), 3.23-3.27 (m, 2H), 3.31-3.35 (t, 2H); $^{13}$CNMR (100 MHz, DMSO-d6) δ 25.80, 25.88, 28.13, 28.87, 32.03, 35.18, 35.24,35.39, 38.31, 38.84, 50.54, 54.89,169.31, 170.04.

Procedure B. Preparation of 32. The mixture of compound 25 (1.00 mmol), EDC (1.50 mmol), and HOBt (1.50 mmol) in $CH_2Cl_2$ (10 mL) was stirred for 1 hr at room temperature. To this solution was added a solution of 26 (3.00 mmoL) and $Et_3N$ (4.00 mmol) in $CH_2Cl_2$ (5 mL) at 0° C. The reaction mixture was then stirred overnight at room temperature. After filtration through a short bed of celite, the organic phase was washed with $H_2O$, $NaHCO_3$, and brine, followed by drying over anhydrous $Na_2SO_4$. Organic solvent was removed under reduced pressure and the crude product was purified by flash chromatography (MeOH/$CH_2Cl_2$: 3/97) to afford 32. $^1$HNMR (400 MHz, $CDCl_3$) δ 0.61 (s, 3H), 0.78-0.80 (dd, J=4.96 Hz, 1.6 Hz, 6H), 0.81-0.83 (d, J=9.44 Hz, 3H), 0.85-2.30 (m, 37H), 3.15-3.26 (m, 3H), 3.89 (s, 2H), 5.28-5.29 (t, J=5.16 Hz, 1H); $^{13}$CNMR (100 MHz, $CDCl_3$) δ 10.84-41.32, 49.12, 50.06, 55.16, 55.73, 66.58, 79.22, 121.31, 139.04, 169.30.

Preparation of 33. Compound 25 (1.00 mmol) was reacted with 27 (3.00 mmol) following Procedure B to give 33. $^1$HNMR (400 MHz, CDCl$_3$) δ 0.61 (s, 3H), 0.78-0.80 (dd, J=4.88 Hz, 1.72 Hz, 6H), 0.83-0.85 (d, J=9.44 Hz, 3H), 0.94-2.30 (41H), 3.14-3.23 (m, 3H), 3.89 (s, 2H), 5.28-5.29 (t, J=5.24 Hz, 1H); $^{13}$CNMR (100 MHz, CDCl$_3$) δ 10.85-41.32, 49.13, 50.35, 55.16, 55.73, 66.62, 79.22, 121.30, 139.07, 169.18.

Preparation of 34. Compound 25 (1.00 mmol) was reacted with 28 (3.00 mmol) following Procedure B to give 34. $^1$HNMR (400 MHz, CDCl$_3$) δ 0.60 (s, 3H), 0.85-0.87 (dd, J=4.92 Hz, 1.68 Hz, 6H), 0.90-0.92 (d, J=6.48 Hz, 3H), 1.00-2.39 (39H), 3.09-3.18 (m, 1H), 3.20-3,25 (m, 4H), 3.48-3.53 (m, 2H), 3.88 (s, 2H), 5.27-5.29 (t, J=5.04 Hz, 1H); $^{13}$CNMR (100 MHz, CDCl$_3$) δ 10.84-41.32, 49.14, 50.03, 55.16, 55.74, 66.50, 79.29, 121.23, 139.12, 169.86, 169.99.

Preparation of 35. Compound 25 (1.00 mmol) was reacted with 29 (3.00 mmol) following Procedure B to give 35. $^1$HNMR (400 MHz, CDCl$_3$) δ 0.67 (s, 3H), 0.85-0.87 (dd, J=4.92 Hz, 1.68 Hz, 6H), 0.90-0.92 (d, J=6.48 Hz, 3H), 1.00-2.43 (43H), 3.16-3.27 (m, 5H), 3.57-3.60 (m, 2H), 3.95 (s, 2H), 5.34-5.35 (t, J=5.04 Hz, 1H); $^{13}$CNMR (100 MHz, CDCl$_3$) δ 11.84-42.32, 50.15, 51.33, 56.16, 56.74, 67.53, 80.29, 122.21, 140.12, 170.81, 170.87.

Preparation of 36. Compound 25 (1.00 mmol) was reacted with 30 (3.00 mmol) following Procedure B to give 36. $^1$HNMR (400 MHz, CDCl$_3$) δ 0.67 (s, 3H), 0.85-0.87 (dd, J=4.92 Hz, 1.68 Hz, 6H), 0.90-0.92 (d, J=6.48 Hz, 3H), 1.00-2.58 (41H), 3.17-3.35 (m, 2H), 3.51-3.59 (m, 3H), 3.70 (s,2H), 3.96 (s, 2H), 5.35-5.36 (t, J=3.28 Hz, 1H); $^{13}$CNMR (100 MHz, CDCl$_3$) δ 10.84-41.31, 49.12, 50.00, 50.79, 55.15, 55.73, 66.56, 79.29, 121.24, 139.09, 169.45, 171.66.

Preparation of 37. Compound 25 (1.00 mmol) was reacted with 31 (3.00 mmol) following Procedure B to give 37. $^1$HNMR (400 MHz, CDCl$_3$) δ 0.67 (s, 3H), 0.85-0.87 (dd, J=4.88 Hz, 1.72 Hz, 6H), 0.90-0.92 (d, J=6.52 Hz, 3H), 1.00-2.58 (45H), 3.16-3.26 (m, 1H), 3.50-3.59 (m, 3H), 3.95-3.96 (d, J=3.56 Hz, 2H), 5.34-5.36 (t, J=5.76 Hz, 1H); $^{13}$CNMR (100 MHz, CDCl$_3$) δ 11.87-42.33, 50.15, 51.81, 51.85, 56.17, 56.75, 67.59, 80.29, 122.20, 140.12, 170.47, 170.73, 171.09.

Procedure C. Preparation of BMAOI 3. To the solution of compounds 32 (1 equivalent) and compound 20 (2 equivalent) in THF/H$_2$O (5 mL, 1:1) was added sodium ascorbate (0.04 equivalent) and CuSO$_4$ (0.02 equivalent) at room temperature. The reaction mixture was stirred for 24 hrs at 65° C. The solvent was removed under reduced pressure and CH$_2$Cl$_2$ (5 mL) was added. The organic layer was washed with H$_2$O and brine, and then dried over anhydrous Na$_2$SO$_4$. After filtration and removal of the solvent under reduced pressure, the crude residue was purified by flash chromatography (MeOH/CH$_2$Cl$_2$: 5/95) to give BMAOI 3 as a yellow solid. $^1$HNMR (400 MHz, CDCl$_3$) δ 0.67 (s, 3H), 0.85-0.87 (dd, J=4.92 Hz, 1.64 Hz, 6H), 0.90-0.91 (d, J=6.48 Hz, 3H), 0.99-2.34 (35H), 3.15-3.21 (m, 1H), 3.30-3.35 (m, 2H), 3.91 (s, 2H), 3.94 (s, 3H), 3.95 (s, 3H), 4.37-4.40 (t, J=14.08 Hz, 2H), 5.32 (s, 2H), 5.32-5.34 (m, 1H), 6.46-6.50 (d, 2H), 6.92-6.94 (d, 1H), 7.05-7.13 (m, 5H), 7.56 (d, 1H), 7.60 (d, 1H), 7.65 (s, 1H); $^{13}$CNMR (100 MHz, CDCl$_3$) δ 11.86-42.32, 49.86-50.11, 55.97-56.72, 63.10, 67.50, 80.21, 101.24, 109.66-128.85, 140.06-149.67, 170.49, 182.92-183.58.

Preparation of BMAOI 9. Compounds 32 (1 equivalent) was reacted with compound 23 (2 equivalent) in THF/H$_2$O (5 mL, 1:1) following Procedure C to give BMAOI 9. $^1$HNMR (400 MHz, CDCl$_3$) δ 0.67 (s, 3H), 0.85-0.87 (dd, J=4.88 Hz, 1.72 Hz, 6H), 0.90-0.92 (d, J=6.52 Hz, 3H), 0.99-2.35 (35H), 3.16-3.28 (m, 3H), 3.39-3.34 (m, 2H), 3.90 (s, 3H), 3.93 (s, 3H), 3.94 (s, 2H), 4.27-4.31 (t, J=14 Hz, 2H), 5.33-5.35 (t, J=5.08 Hz, 1H), 6.64-6.68 (d, 2H), 6.88-6.91 (m, 3H), 6.92-7.09 (m, 4H), 7.58-7.62 (d, 1H), 7.68-7.72 (d, 1H); $^{13}$CNMR (100 MHz, CDCl$_3$) δ 11.86-42.33, 49.67-50.12, 56.04-56.73, 63.07, 67.48, 80.22, 108.87, 109.83-128.88, 140.09-149.67, 170.51, 182.12, 194.47.

Preparation of BMAOI 4. Compounds 33 (1 equivalent) was reacted with compound 20 (2 equivalent) in THF/H$_2$O (5 mL, 1:1) following Procedure C to give BMAOI 4. $^1$HNMR (400 MHz, CDCl$_3$) δ 0.67 (s, 3H), 0.85-0.87 (dd, J=4.88 Hz, 1.72 Hz, 6H), 0.90-0.91 (d, J=6.52 Hz, 3H), 1.00-2.34 (39H), 3.21-3.29 (m, 3H), 3.91 (s, 2H), 3.94 (s, 3H), 3.95 (s, 3H), 4.31-4.35 (t, J=14.36 Hz, 2H), 5.33 (s, 2H), 5.33 (t, 1H), 6.46 (d, 1H), 6.50 (d, 1H), 6.92-6.94 (d, 1H), 7.05-7.13 (m,5H), 7.56-7.57 (d, 1H), 7.60-7.61 (d,1H), 7.62 (s, 1H); $^{13}$CNMR (100 MHz, CDCl$_3$) δ 11.86-42.33, 50.11-50.32, 55.98-56.72, 63.10, 67.59, 80.22, 101.24, 109.66-128.85, 140.06-149.67, 170.26, 182.92-183.56.

Preparation of BMAOI 10. Compounds 33 (1 equivalent) was reacted with compound 23 (2 equivalent) in THF/H$_2$O (5 mL, 1:1) following Procedure C to give BMAOI 10. $^1$HNMR (400 MHz, CDCl$_3$) δ 0.60 (s, 3H), 0.85-0.87 (dd, J=4.88 Hz, 1.72 Hz, 6H), 0.90-0.91 (d, J=6.52 Hz, 3H), 0.99-2.44 (39H), 3.07-3.18 (m, 3H), 3.31-3.33 (m, 4H), 3.82 (s, 3H), 3.84 (s, 3H), 3.89 (s, 2H), 4.16-4.18 (t, J=11.92 Hz, 2H), 5.27-5.28 (t, J=5.16 Hz, 1H), 6.58-6.62 (d, 1H), 6.79-6.83 (m, 2H), 6.92-7.00 (m, 4H), 7.24 (s, 1H), 7.49-7.53 (d, 1H), 7.60-7.64 (d, 1H); $^{13}$CNMR (100 MHz, CDCl$_3$) δ 10.84-41.31, 49.11-50.15, 55.01-55.71, 62.90, 66.55, 79.24, 108.87, 109.92-128.88, 140.09-149.67, 170.26, 182.12, 193.57.

Preparation of BMAOI 5. Compounds 34 (1 equivalent) was reacted with compound 20 (2 equivalent) in THF/H$_2$O (5 mL, 1:1) following Procedure C to give BMAOI 5. $^1$HNMR (400 MHz, CDCl$_3$) δ 0.66 (s, 3H), 0.84-0.87 (dd, J=4.96 Hz, 1.64 Hz, 6H), 0.89-0.91 (d, J=6.48 Hz, 3H), 0.98-2.43 (37H), 3.15-3.2 (m, 1H), 3.26 (m, 2H), 3.55-3.57 (m, 4H), 3.91 (s, 2H), 3.93 (s, 6H), 4.36 (t, 2H), 5.33 (s, 2H), 5.33 (t, 1H), 6.48 (d, 2H), 6.93-6.19 (m, 5H), 7.57-7.6610 (m, 3H); $^{13}$CNMR (100 MHz, CDCl$_3$) δ 11.86-42.33, 49.86-50.14, 55.98-56.73, 63.02, 67.47, 80.30, 101.26, 109.79-128.93, 140.10-149.68, 170.09-171.23, 182.85-183.64.

Preparation of BMAOI 11. Compounds 34 (1 equivalent) was reacted with compound 23 (2 equivalent) in THF/H$_2$O (5 mL, 1:1) following Procedure C to give BMAOI 11. $^1$HNMR (400 MHz, CDCl$_3$) δ0.67 (s, 3H), 0.85-0.87 (dd, J=4.92 Hz, 1.68 Hz, 6H), 0.90-0.91 (d, J=6.56 Hz, 3H), 0.99-2.44 (37H), 3.07-3.11 (m, 1H), 3.17-3.19 (m, 4H), 3.53-3.57 (m, 2H), 3.90 (s, 2H), 3.92 (s, 3H), 3.95 (s, 3H), 4.26-4.29 (t, J=13.72 Hz, 2H), 5.33-5.34 (t, J=2.88 Hz, 1H), 6.66-6.67 (d, 1H), 6.89-6.92 (m, 3H), 6.99-7.09 (m, 4H), 7.22 (s, 1H), 7.57-7.61 (d, 1H), 7.67-7.70 (d, 1H); $^{13}$CNMR (100 MHz, CDCl$_3$) δ 11.87-42.34, 49.64-50.15, 56.07-56.75, 62.90, 67.49, 80.32, 108.87, 109.92-128.88, 140.09-149.67, 170.01-171.13, 182.12, 194.55.

Preparation of BMAOI 6. Compounds 35 (1 equivalent) was reacted with compound 20 (2 equivalent) in THF/H$_2$O (5 mL, 1:1) following Procedure C to give BMAOI 6. $^1$HNMR (400 MHz, CDCl$_3$) δ 0.67 (s, 3H), 0.85-0.87 (dd, J=5 Hz, 1.6 Hz, 6H), 0.90-0.91 (d, J=6.52 Hz, 3H), 0.99-2.44 (41H), 3.18-3.21 (m, 3H), 3.57-3.58 (m, 4H), 3.91 (s, 2H), 3.94 (s, 6H), 4.32-4.35 (t, J=14.16 Hz, 2H), 5.33 (s, 2H), 5.33 (t, 1H), 6.46-6.47 (d, 1H), 6.50-6.51 (d, 1H), 6.92-6.94 (d, 1H), 7.05-7.19 (m, 5H), 7.56-7.57 (d, 1H), 7.60-7.61 (d, 1H), 7.62 (s, 1H); $^{13}$CNMR (100 MHz, CDCl$_3$) δ 11.86-42.33, 50.13-50.23, 55.98-56.74, 63.09, 67.52, 80.29, 101.25, 109.68-128.87, 140.09-149.67, 170.01-171.23, 182.95-183.55.

Preparation of BMAOI 12. Compounds 35 (1 equivalent) was reacted with compound 23 (2 equivalent) in THF/H$_2$O (5 mL, 1:1) following Procedure C to give BMAOI 12. $^1$HNMR (400 MHz, CDCl$_3$) δ 0.67 (s, 3H), 0.80-0.87 (dd, J=4.92 Hz, 1.68, 6H), 0.90-0.91 (d, J=6.64 Hz, 3H), 0.93-2.35 (41H), 3.03-3.22 (m, 3H), 3.38-3.40 (d, 1H), 3.53-3.67 (m, 3H), 3.90 (s, 2H), 3.94 (s, 3H), 3.96 (s, 3H), 4.22-4.27 (t, J=14.88 Hz, 2H), 5.33-5.34 (t, J=3.48, 1H), 6.65-6.69 (d, 1H), 6.89-6.91 (d, 2H), 6.98-7.09 (m, 4H), 7.20 (s, 1H), 7.55-7.59 (d, 1H), 7.67-7.71 (d, 1H); $^{13}$CNMR (100 MHz, CDCl$_3$) δ 11.87-42.34, 50.14-50.19, 56.06-56.75, 63.06, 67.49, 80.33, 108.87, 109.88-128.88, 140.09-149.67, 170.01-171.23, 182.12, 194.62.

Preparation of BMAOI 7. Compounds 36 (1 equivalent) was reacted with compound 20 (2 equivalent) in THF/H$_2$O (5 mL, 1:1) following Procedure C to give BMAOI 7. $^1$HNMR (400 MHz, CDCl$_3$) δ 0.67 (s, 3H), 0.85-0.87 (d, J=6.44 Hz, 6H), 0.90-0.91 (d, J=6.48 Hz, 3H), 0.98-2.4 (39H), 3.20-3.28 (m, 3H), 3.52-3.56 (m, 4H), 3.91 (s, 2H), 3.94 (s, 3H), 3.96 (s, 3H), 4.36-4.39 (t, J=13.56 Hz, 2H), 5.31 (s, 2H), 5.34 (t, 1H), 6.46-6.47 (d, 1H), 6.50-6.51 (d, 1H), 6.92-6.94 (d, 1H), 7.05-7.13 (m, 5H), 7.56-7.57 (d, 1H), 7.60-7.61 (d, 1H), 7.67 (s, 1H); $^{13}$CNMR (100 MHz, CDCl$_3$) δ 11.86-42.33, 50.12-50.19, 55.98-56.73, 63.06, 67.57, 80.33, 101.26, 109.71-128.88, 140.09-149.67, 170.01-171.23, 182.85-183.64.

Preparation of BMAOI 13. Compounds 36 (1 equivalent) was reacted with compound 23 (2 equivalent) in THF/H$_2$O (5 mL, 1:1) following Procedure C to give BMAOI 13. $^1$HNMR (400 MHz, CDCl$_3$) δ 0.67 (s, 3H), 0.82-0.87 (dd, J=4.88 Hz, 1.72 6H), 0.90-0.91 (d, J=6.52 Hz, 3H), 0.93-2.4 (39H), 3.17-3.20 (m, 3H), 3.38-3.55 (m, 6H), 3.90 (s, 2H), 3.92 (s, 3H), 3.95 (s, 3H), 4.24-4.30 (t, J=13.44 Hz, 2H), 5.33-5.34 (t, 1H), 6.65-6.67 (d, 1H), 6.69-6.71 (d, 1H), 6.89-6.91 (d, 1H), 7.00-7.09 (m, 5H), 7.57-7.61 (d, 1H), 7.67-7.71 (d, 1H), 7.63 (s, 1H); $^{13}$CNMR (100 MHz, CDCl$_3$) δ 11.86-42.33, 50.12-50.19, 56.07-56.73, 63.06, 67.57, 80.33, 108.87, 109.71-128.88, 140.09-149.67, 170.01-171.23, 182.12, 193.57.

Preparation of BMAOI 8. Compounds 37 (1 equivalent) was reacted with compound 20 (2 equivalent) in THF/H$_2$O (5 mL, 1:1) following Procedure C to give BMAOI 8. $^1$HNMR (400 MHz, CDCl$_3$) δ 0.67 (s, 3H), 0.85-0.87 (dd, J=4.92 Hz, 1.68 Hz, 6H), 0.90-0.91 (d, J=6.52 Hz, 3H), 0.93-2.4 (43H), 3.17-3.22 (m, 3H), 3.48-3.56 (m, 4H), 3.89 (s, 2H), 3.94 (s, 3H), 3.96 (s, 3H), 4.36-4.39 (t, J=12 Hz, 2H), 5.33 (s, 2H), 5.33 (t, 1H), 6.45-6.47 (d, 1H), 6.49-6.51 (d, 1H), 6.92-6.94 (d, 1H), 7.05-7.12 (m, 5H), 7.55-7.57 (d, 1H), 7.59-7.61 (d, 1H), 7.63 (s, 1H); $^{13}$CNMR (100 MHz, CDCl$_3$) δ 11.86-42.32, 50.13-50.19, 55.98-56.73, 63.06, 67.57, 80.29, 101.26, 109.71-128.88, 140.09-149.67, 170.01-171.23, 182.85-183.64.

Preparation of BMAOI 14. Compounds 37 (1 equivalent) was reacted with compound 23 (2 equivalent) in THF/H$_2$O (5 mL, 1:1) following Procedure C to give BMAOI 14. $^1$HNMR (400 MHz, CDCl$_3$) δ 0.67 (s, 3H), 0.85-0.87 (dd, J=4.88 Hz, 1.56 Hz 6H), 0.90-0.91 (d, J=6.52 Hz, 3H), 0.93-2.4 (43H), 3.17-3.22 (m, 3H), 3.48-3.56 (m, 6H), 3.89 (s, 2H), 3.94 (s, 3H), 3.96 (s, 3H), 4.32-4.36 (t, J=13.96 Hz, 2H), 5.33 (t, 1H), 6.45-6.47 (d, 1H), 6.49-6.51 (d, 1H), 6.92-6.94 (d, 1H), 7.05-7.12 (m, 5H), 7.56-7.57 (d, 1H), 7.59-7.61 (d, 1H), 7.63 (s, 1H); $^{13}$CNMR (100 MHz, CDCl$_3$) δ 11.86-42.32, 50.13-50.19, 55.98-56.73, 63.06, 67.57, 80.29, 108.87, 109.71-128.88, 140.09-149.67, 170.01-171.23, 182.12, 193.57.

Biological assays. Aβ42 was obtained from American Peptide, Inc. (Sunnyvale, Calif.). 6E10 antibody was obtained from Signet (Dedham, Mass.). A11 oligomer Rabbit polyclonal antibody, Alexa Fluor 568 donkey anti-rabbit IgG, Alexa 488 conjugated cholera toxin subunit B (CTX-B) were obtained from Invitrogen (CA, USA). 4',6-diamidino-2-phenylindole (DAPI) was obtained from Sigma-Aldrich (St. Louis, Mo.).

MC65 cells were cultured in Dulbecco's Modified Eagle's Medium (DMEM) (Life Technologies, Inc., Grand Island, N.Y.) supplemented with 10% of heat-inactivated fetal bovine serum (FBS) (Hyclone, Logan, Utah), 1 μg/mL TC and 0.2 mg/mL G418 (Invitrogen) and maintained at 37° C. in a fully humidified atmosphere containing 5% $CO_2$. SH-SY5Y neuroblastoma cells were obtained from American Type Culture Collection (ATCC) and were cultured in DMEM/Ham's F-12 (Invitrogen) supplemented with 10% FBS. ML60 cells were maintained in DMEM supplemented with 10% FBS, 0.2 mg/mL G418, and 25 μg/mL puromycin. All experiments were performed on 70% confluent growing cells unless otherwise indicated.

Western blot assay. MC65 cells were seeded in 6-well plates (1×10$^6$ cells/well). After incubation at 37° C., 5% $CO_2$ for 24 hrs, the medium was replaced with fresh Opti-MEM (Invitrogen) and compounds in Opti-MEM (with or without TC) were added. After 24 hrs incubation, cells were collected on ice and centrifuged. Pellet was lysed by sonication in 1× lysis buffer (62.5 mM Tris base, pH6.8, 2% SDS, 50 mM DTT, 10% glycerol, 0.1% bromphenol blue, and 5 mg/ml each chymostatin, leupeptin, aprotinin, pepstatin, and soybean trypsin inhibitor) and protein level was determined using Coomassie Protein Assay Reagent (Pierce, Rockford, Ill.). Equal amounts of protein (10 μg) were separated by SDS-PAGE on 10-20% tris-tricine gel (Bio-Rad) and transferred onto a PVDF membrane (Bio-Rad). The blots were blocked with 5% milk in TBS-Tween 20 (0.1%) at room temperature for 1 hr and probed with primary 6E10 (1:2000) antibody overnight at 4° C. The blots were then incubated with horseradish peroxidase-conjugated secondary antibody (1:2000. Kirkegaard & Perry, Gaithersburg, Md.). The proteins were visualized by Western Blot Chemiluminescence Reagent (NEN Life Science Products, Boston, Mass.).

Immunocytochemistry assay. MC65 cells were plated onto Lab-Tec chamber slides (1×10$^4$ cells/well). After 24 hrs incubation at 37° C. and 5% $CO_2$, Opti-MEM was added (with or without TC) and followed by test compounds. MC65 cells were incubated for 24 hrs. MC65 cells were rinsed 3× with PBS and incubated with Alexa 488-conjugated CTX-B (10 ug/mL) for 15 min on ice. After rinsing once with ice-cold PBS, cells were fixed for 30 min with 4% paraformaldehyde. MC65 cells were permeabilized for 30 min with 0.1% Triton X 100. Then MC65 cells were stained with A11 rabbit antibody followed by anti-rabbit Alexa 568 (1:500). Finally MC65 cells were treated with DAPI (5 ug/mL) and mounted with Vectashield Mounting Media. Cell fluorescence was analyzed by a Leica TCS-SP2 AOBS confocal laser scanning microscope equipped with blue diode, Argon, and 3 HeNe (lasers as well as a spectrophotometer based detection system with variable detector windows) using excitation lines at 355 nm, 488 nm, and 568 nm for DAPI, Alexa 488-conjugated CTX-B, and Alexa Fluor 568 donkey anti-rabbit IgG. Sequential scanning was conducted to insure that there was no signal cross-talk between channels. Five different areas around the center were taken and the red puncta was averaged per cell.

For BMAOI 14 interaction with CM/LR immunocytochemistry assay, MC65 cells were incubated with 1 or 14 for 24 hrs, then fixed with 4% paraformaldehyde and permeabilized with 0.1% Triton X 100. MC65 cells were incubated with DAPI and mounted with Vectashield Mounting Media for confocal laser scanning using excitation lines at 355 nm and 494 nm. A series of optical sections (1024×1024 pixels)

of 1.0 μm in thickness were taken through the cell depth for examined sample and projected as a single composite image by superimposition.

Aβ42 oligomerization inhibition assay. An aliquot of Aβ42 (0.045 mg) was dissolved in 20 μL of DMSO and diluted in Ham's F-12 media without phenol red (Caisson's Laboratory, Inc., Utah). Aβ42 (5 βM) was incubated with 1 or 14 (20 μM) in 37° C. water bath for 4 hrs. After incubation, the samples (50 μL) were spun down at 14,000×g for 10 min. The supernatant (20 μL) was mixed with an equal part of Tricine sample buffer without reducing agents (Bio-Rad). The unaggregated Aβ42 control was not incubated at 37° C., and mixed with sample buffer (no centrifuging) and stored at −80° C. before it was electrophoresed. Samples (25 μL) were electrophoresed on a 10-20% Tris-Tricine gel, transferred to PVDF membrane, and blocked with 10% nonfat milk in PBS for 30 min. The blots were probed with 6E10 (1:2000) overnight at 4° C., followed by horseradish peroxidase-conjugated secondary antibody (1:2000. Kirkegaard & Perry, Gaithersburg, Md.). The proteins were visualized by Western Blot Chemiluminescence Reagent (NEN Life Science Products, Boston, Mass.).

Transmission electron microscope (TEM). 10 μL of Aβ42 in Ham's F-12 (20 μM) were adsorbed onto 200-mesh carbon and formavar-coated grids (Electron Microscopy Sciences) for 20 min, washed for 1 min in distilled $H_2O$. The samples were negatively stained with 2% uranyl acetate (Electron Microscopy Sciences) for 5 min and washed for 1 min in distilled $H_2O$. The samples were air-dried overnight and viewed with a Jcol JEM-1230 TEM equipped with a Gatan UltraScan 4000SP 4K×4K CCD camera (100 kV).

Cytotoxicity assay in MC65 cells. MC65 cells were seeded in 96-well plates ($4 \times 10^4$ cells/well) at 37° C., 5% CO2 for 24 hrs. The medium was removed and washed with PBS twice. Opti-MEM and test compounds were added under +TC and −TC conditions. The plates were incubated at 37° C., 5% $CO_2$ for 72 hrs, then 20 uL CellTiter 96 $AQ_{ueous}$ One Solution (Promega, Madison, Wis.) were added to each well and the plates were incubated at 37° C., 5% $CO_2$ for 2-4 hrs. The plates were read at 490 nm using FlexStation III plate reader (Molecular Devices). The blank with only test compounds in Opti-MEM was set up as background control for all of the tested concentrations. Each data point was averaged from six replicates and the experiments were independently repeated at least three times.

Cytotoxicity assay in differentiated SH-SY5Y cells. SH-SY5Y cells were plated at 10,000 cells/well in type 1 collagen coated 96-well plates (Invitrogen) and were differentiated in Opti-MEM supplemented with 2% B-27 (Invitrogen) and 10 μM all-trans-retinoic acid for 7 days. The medium was removed and replaced with fresh maintenance medium. Freshly prepared Aβ42 oligomers in Ham's F-12 medium (1 μM) was added to cells for 48 hrs at 37° C. with or without test compounds. After treatment, 20 uL CellTiter 96 $AQ_{ueous}$ One Solution (Promega, Madison, Wis.) were added to each well and the plates were incubated at 37° C., 5% $CO_2$ for 2-4 hrs. The plates were read at 490 nm in FlexStation III plate reader (Molecular Devices). Each data point was averaged from six replicates and the experiments were independently repeated at least three times.

ML60 cell assay. Sandwich enzyme-linked immunoassays (ELISAs) for extracellular AβOs in ML60 cells were performed. ML60 cells (90% confluent) in 96-well plates were treated with test compounds (10 μM) at 37° C., 5% $CO_2$ for 24 hrs. ML60 cells were centrifuged for 5 min at 6000 g, and supernatant media was collected for AβOs measurement by ELISA. The capture antibody 21F12 (to Aβ residues 33-42) was used for capturing both monomeric and oligomeric Aβ42 species. The detecting antibody was biotinylated 21F12B, and the combination of 21F12 and biotinylated 21F12B allows the detection of only AβOs. The 21F12 mAbs were coated at 10 mg/mL into 96-well immunoassay plates (Costar) at room temperature overnight. The plates were then aspirated and blocked with 0.25% human serum albumin in PBS buffer for 1 hr at room temperature. The plates were rehydrated with wash buffer (0.05% Tween 20 in TBS) before use. The samples were added to the plates and incubated at room temperature for 1 hr. The plates were washed 3× with wash buffer between each step of the assay. The biotinylated 21F12B diluted to 0.5 mg/mL in casein assay buffer (0.25% casein, 0.05% Tween 20, pH 7.4, in PBS), was incubated in the wells for 1 hr at room temperature. Avidin-horseradish peroxidase (Vector Laboratories), diluted 1:4000 in casein assay buffer, was added to the wells for 1 hr at room temperature. The colorimetric substrate, Slow TMB-ELISA (Pierce), was added and allowed to react for 15 min, after which the enzymatic reaction was stopped with addition of 1 M $H_2SO_4$. Reaction product was quantified using plate reader by measuring the difference in absorbance at 450 nm and 650 nm.

Anti-CD3 antibody mediated splenocyte proliferation. A single spleen cell suspension from female B6C3F1 mice (N=4) was prepared and resuspended in RPMI medium supplemented with FBS (10%), sodium bicarbonate (GIBCO), HEPES (GIBCO), L-glutamine, gentamicin and 2-mercaptoethanol (0.00035%). The splenocytes ($2 \times 10^5$/well) were cultured in the microtiter wells coated with anti-CD3 Ab (1 μg/mL; BD PharMingen) in the presence of 1 or 14 (10 μM) at 37° C. in 5% $CO_2$. Prior to harvest on day 3, the cells were pulsed with $^3$H-thymidine for 18-24 hours. The incorporation of $^3$H-thymidine into the proliferating cells was used as the endpoint of the assay, and the data were expressed as $CPM/2 \times 10^5$ cells.

IL-2 augmented natural killer (NK) cell activity. To determine NK activity, single cell suspensions from female B6C3F1 mice (N=4) were adjusted to $2.5 \times 10^6$ cells/mL in a 96-well U-bottom plate (0.1 mL/well) for each animal. Recombinant IL-2 (Chiron, Emeryville, Calif.) at a volume of 50 μL was added to each well so that the final concentration of IL-2 was 5000 fU/mL. The plates were cultured overnight in the presence of 1 or 14 (10 μM), and then assayed for NK cell activity using $^{51}$Cr-labeled YAC-1 cells as the target cells. The $^{51}$Cr-YAC-1 cells were added to each well of a 96-well plate to obtain E:T ratio of 50:1. The spontaneous release and the maximum release were determined by adding 0.1 mL of medium and Triton X-100 (0.1%) to each of 12 replicate wells containing the target cells, respectively. Following 4 hrs incubation, the plates were centrifuged, and 0.1 mL of the supernatant was removed from each well and the radioactivity counted. The mean percentage of cytotoxicity was determined.

DCFH-DA antioxidation assay. MC65 cells were seeded in 96-well plates ($4 \times 10^4$ cells/well). After incubation at 37° C., 5% $CO_2$ for 24 hrs, the medium was removed and washed with PBS. Opti-MEM and test compounds were added (+TC, −TC, and blank with only test compounds). MC65 cells were incubated at 37° C., 5% $CO_2$ for 24 hrs. Then DCFH-DA in Opti-MEM was added to each well (final DCFH-DA concentration was 25 uM) and incubate at 37° C., 5% $CO_2$ for 30 min. The medium was removed and replaced with fresh opti-MEM and plates were read for fluorescence intensity at 485 nm (excitation)/530 nm (emission) using FlexStation III plate reader (Molecular Devices).

Caco-2 permeability assay. Caco-2 cells (ATCC, Manassas, Va.) were cultured in high-glucose DMEM supplemented with 10% FBS and used between passages 30-50. Caco-2 cells were plated on 12-well polyester transwell inserts (0.4 µM pore size) (Corning #3460) at a density of 80,000 cells/$cm^2$ and grown to 100% confluence (21 days). Filters were rinsed in Hank's balanced salt solution (HBSS) and test compounds (10 µM) were added to either the apical (0.5 mL) or basolateral (1.5 mL) side and incubated at 37° C. with shaking (100 rpm). Samples (200 µL) were removed at 30, 60, and 120 minutes with replacement of an equal volume of the appropriate buffer containing or lacking the compounds. Samples were stored at −20° C. until analysis. After 120 minutes, lucifer yellow was added to the donor chamber, with additional sampling as above at 10, 20, and 30 minutes. Lucifer yellow was analyzed by fluorescence (excitation 450 nm, emission 528 nm) in a Synergy 2 microplate reader. Monolayer tight junctions and integrity were confirmed by measurement of transepithelial electrical resistances >400 ohm.$cm^2$ and by lucifer yellow permeabilities of <1×10$^{-6}$ cm/sec. Buffer samples (200 µL) were mixed with acetonitrile (100 µL) and acetic acid (2 µL), vortexed and centrifuged at 4° C. for 5 minutes at 12,000 ref. Supernatants (100 µL) were injected onto an Alltech Alltima HP C18 4.6×100 mm 3 µm column and eluted with 38% acetonitrile, 62% aqueous (1% acetic acid in water) at 1.0 mL/min. To improve sensitivity over UV detection, fluorescence (Waters 2475) at the excitation/emission wavelengths of 443/533 and 274/305 (nm) for 1 and 14, respectively, was also detected. Permeability was determined according to Fick's Law. Efflux transport activity was defined as a permeability directional ratio (efflux ratio) ≥2.

Example 2

Bivalent Ligands Containing Curcumin and Cholesterol as Fluorescence Probe for Aβ Plaques in Alzheimer's Disease ABSTRACT: A recently developed bivalent ligand 14 has been evaluated for its capability to label and detect aggregated β-amyloid (Aβ) peptide as a fluorescence probe. This probe contains curcumin as the Aβ recognition moiety and cholesterol as an anchorage to the neuronal cell membrane/lipid rafts. The results demonstrate that 14 binds to the monomers, oligomers as well as fibril of Aβ42 with low micomolar to submicromolar binding affinities. This chemical probe has also required optical properties and can rapidly cross the blood-brain barrier (BBB). Furthermore, 14 fluorescently stain Aβ plaques in transgenic mouse brain tissue. Collectively, these results suggest that 14 may be developed as an Aβ-imaging agent and encourage further optimization of 14 as a new hit to develop better fluorescent probes.

Alzheimer's disease (AD[a]) is a devastating neurodegenerative disease and is the most common cause of dementia. One of the pathological hallmarks is characterized by the presence of β-amyloid (Aβ) plaques in the brain of AD patients with the major components being Aβ40 and Aβ42 peptides.[1] Clinical diagnosis of late-stage AD is based on cognition and behavioral tests of patients[58] and definitive diagnosis is only achieved by postmortem examination to show the presence of Aβ plaques and neurofibrillary tangles, another pathological hallmark of AD.[1] Even though the etiology of AD still remains elusive, Aβ hypothesis has gained extensive attention and numerous studies have established a correlation of the Aβ aggregates (oligomers and fibrils) and cognitive impairment associated with AD.[3] Therefore, Aβ represents an attractive target to develop labeling and imaging probes to help monitor the progression of the disease as well as to achieve the early detection of AD, thus significantly reducing the social and economic burden caused by this disease.

Figure 6:
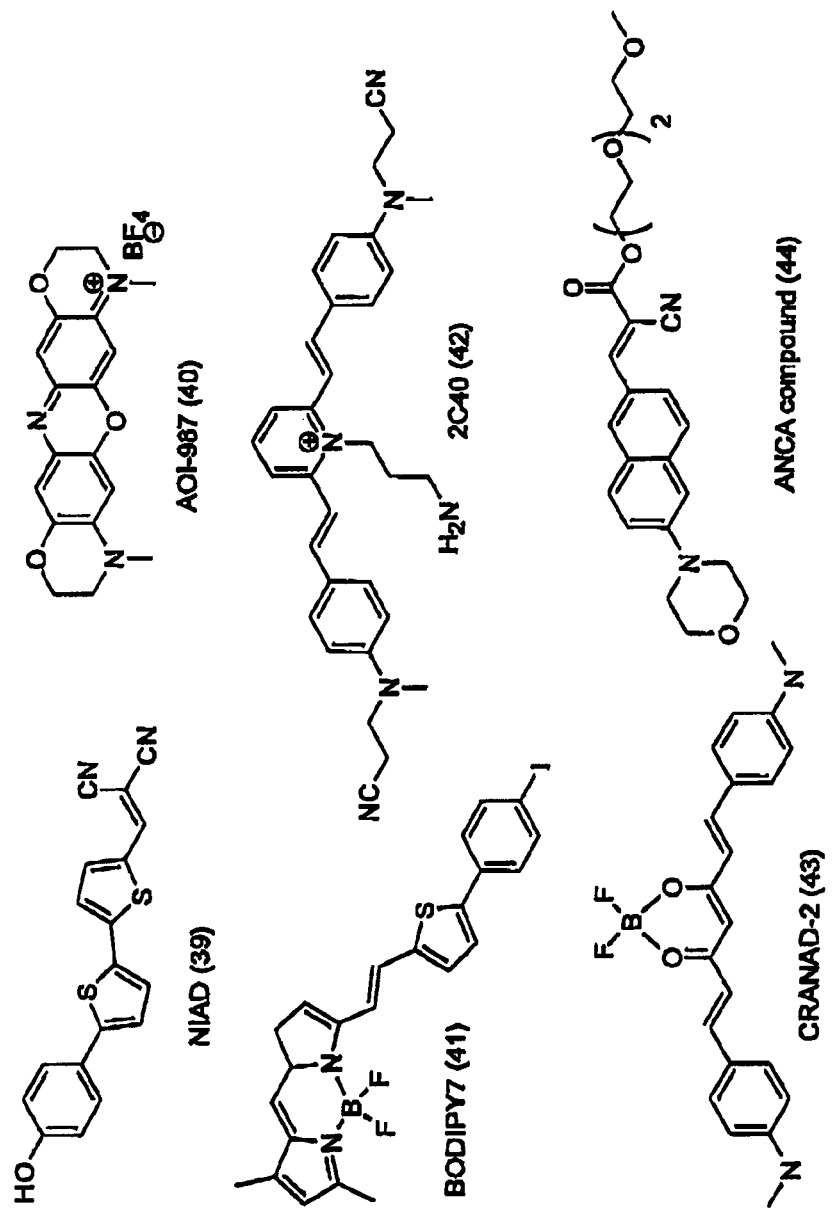
FIG. 6. Representative fluorescence probes that stain Aβ plaques.

Many probes have been developed to date for the specific imaging of Aβ plaques by employing techniques such as magnetic resonance imaging (MRI),[59,60] positron emission tomography (PET), single photon emission computed tomography (SPECT), and multiphoton microscopy.[61,62] Although studies employing these probes produced promising results in in vitro, ex vivo and small animal experiments, further clinical development is limited due to several factors associated with these techniques. These include poor spatial resolution, low sensitivity, exposure to radioactivity, short-lived isoptopes, and invasive methodology, among others. In search of new chemical probes to overcome these problems, fluorescent probes have gained growing interests in this field recently as non-invasive alternative for labeling and imaging Aβ plaques.[63-70] Ideally, a fluorescent probe should have the following properties to be useful in clinics: 1) specificity to Aβ plaques; 2) high binding affinity to aggregated Aβ; 3) ability to rapidly cross the blood-brain barrier (BBB); 4) emission wavelength above 450 nm to minimize background fluorescence and a large Stokes shift; and 5) a significant change in fluorescence properties upon binding to aggregated Aβ. Several fluorescent probes have been developed to meet some of these properties as the proof-of-principle of this methodology (FIG. 6) and studies of these fluorescent probes demonstrated promising results in labeling and imaging Aβ plaques,[63-70] thus attesting to the clinical application of these probes.

Figure 7:
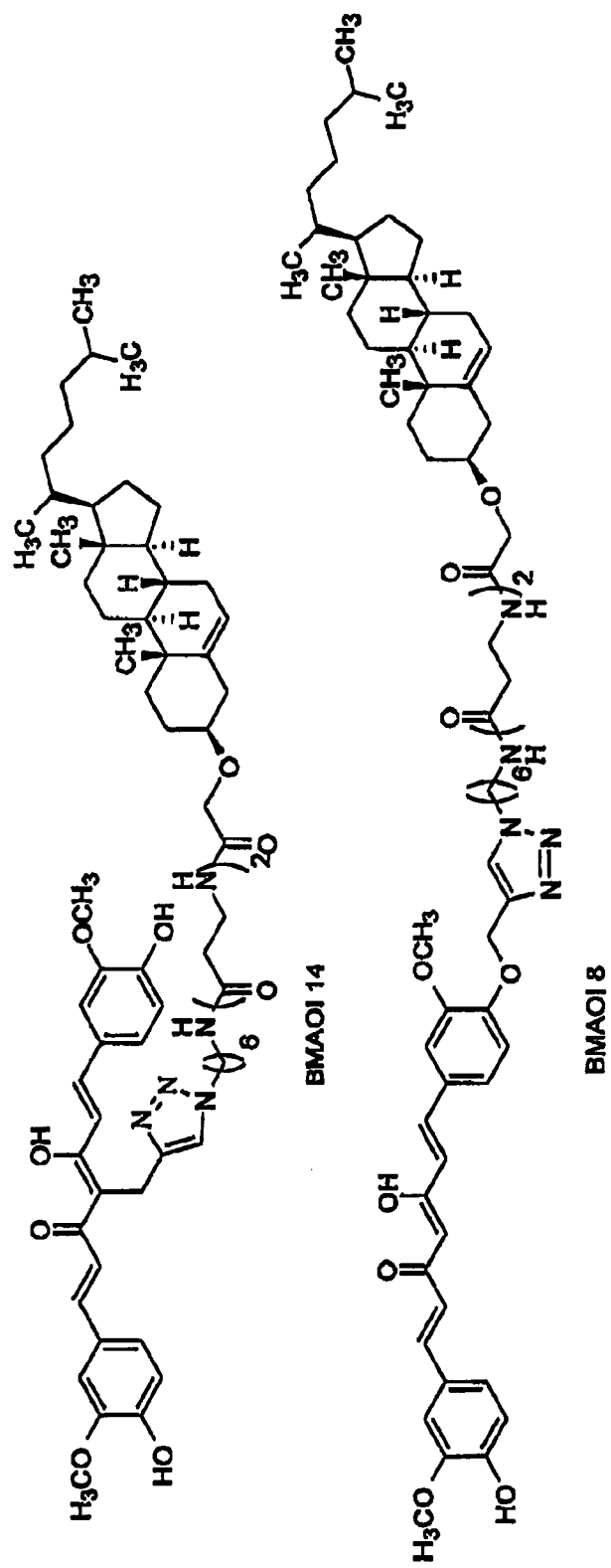
FIG. 7. Chemical structures of BMAOI 14 and BMAOI 8.

Example 1 describes the rational design and development of bivalent multifunctional Aβ oligomerization inhibitors (BMAOIs) as potential AD treatments by incorporating the cell membrane/lipid rafts anchorage into molecular design.[71] These BMAOIs contain curcumin as Aβ recognition and multifunctional moiety on one end and cholesterol as cell membrane/lipid rafts anchorage on the other end. One compound with a 21-atom spacer, 14, was discovered to have favorable pharmacological properties and to bind Aβ oligomers (FIG. 7). Given the fact that this bivalent ligand bears intrinsic fluorescence due to the curcumin fluorophore in the molecule and curcumin derivatives have been developed as PET and fluorescent probes,[66,72] this compound may be explored as potential fluorescent probe to label and detect Aβ plaques. Herein, we present results to show that 14 possess optical properties and Aβ binding affinity that meet some of the required properties as a fluorescent probe. In addition, staining of Aβ plaques in transgenic mouse brain tissue and rapid BBB penetration of this compound are also confirmed.

Results and Discussion

Figure 8A:
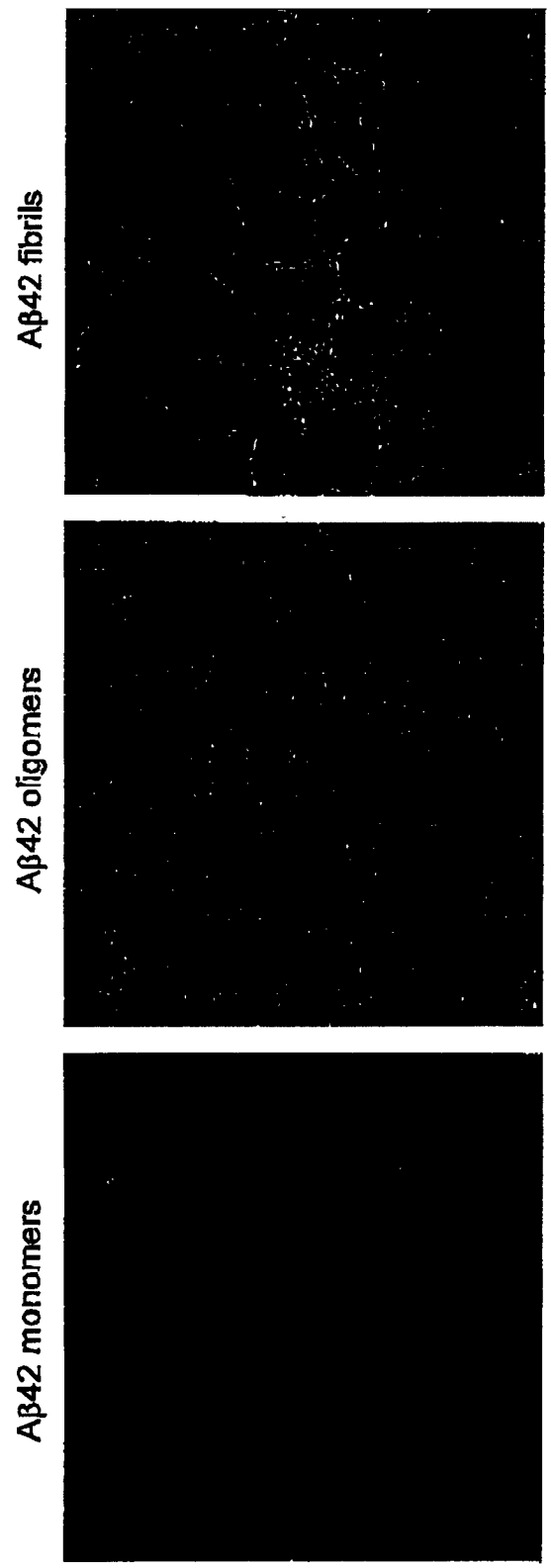
FIG. 8A-C. BMAOI 14 binds to Aβ42 monomers, oligomers, and fibrils, but not BSA. A. The monomers, oligomers and fibrils of Aβ42 were prepared according to established protocols and confirmed by TEM; B. Compound 14 (1 μM) was incubated with different forms of Aβ42 at indicated concentrations for 3 hrs. Then, fluorescence polarization change of 14 was recorded and the binding affinity was calculated; C. Compound 14 was incubated with BSA as described in B and the binding affinity was calculated.
Figures 8B, 8C:
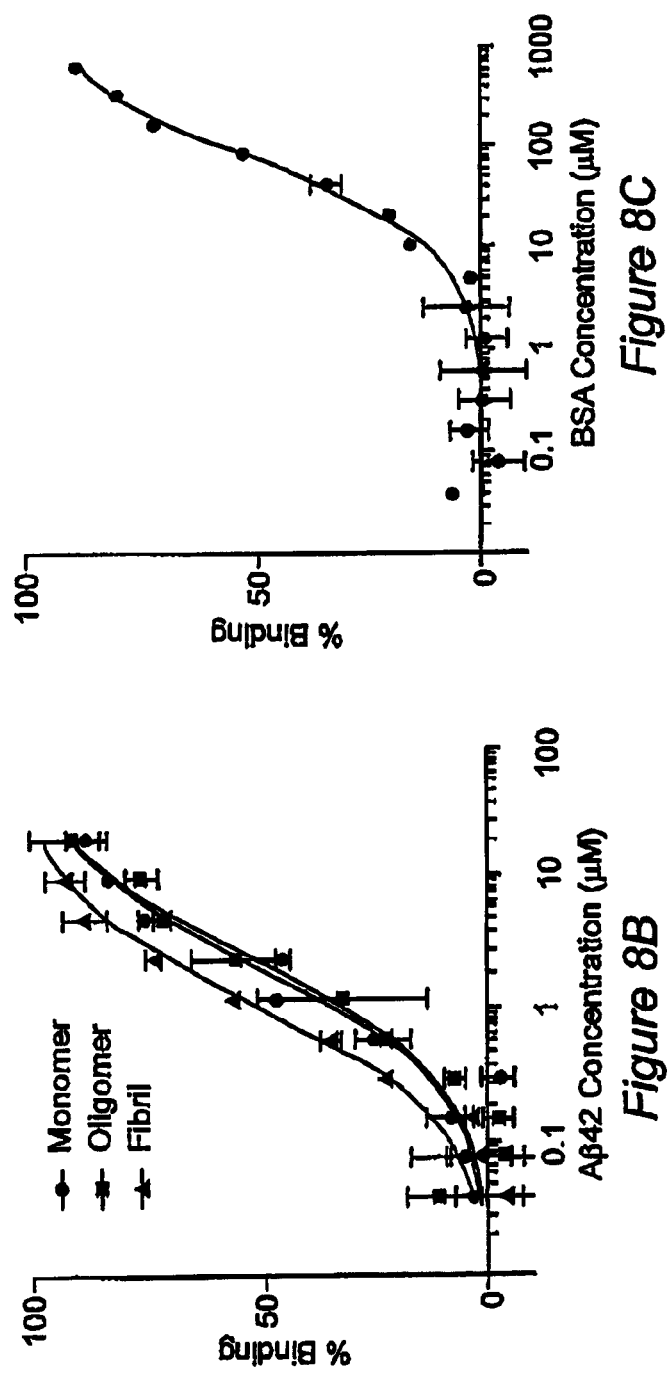

To determine the binding affinity of 14 to Aβ, we evaluated changes in fluorescence polarization values of this probe at different 14:Aβ ratios for monomeric, oligomeric, and fibrillary Aβ species, respectively. Aβ42 is chosen to evaluate the binding of probe as it is the major and most sticky amyloid peptide found in AD plaques.[1] The formation of different Aβ42 species was confirmed by transmission electron microscope (TEM) as shown in FIG. 8A. As seen in FIG. 8B, the apparent binding constants ($K_d$) of 14 for monomers, oligomers, and fibrils of Aβ42 are 2.03, 2.17, and 0.83 uM, respectively. It appears that 14 binds to Aβ42 with micromolar affinity and slightly favors Aβ2 fibrils over monomers and oligomers. Next, we tested the binding affinity of this molecular probe with bovine serum albumin (BSA) as low BSA binding has been suggested as one of the required properties as ideal fluorescent probes. As shown in FIG. 8C, the binding affinity of 14 to BSA is significantly less than the binding affinity to Aβ42 ($K_d$~120 µM), thus suggesting that the interference from serum albumin will be minimal for this probe.

Figure 9:
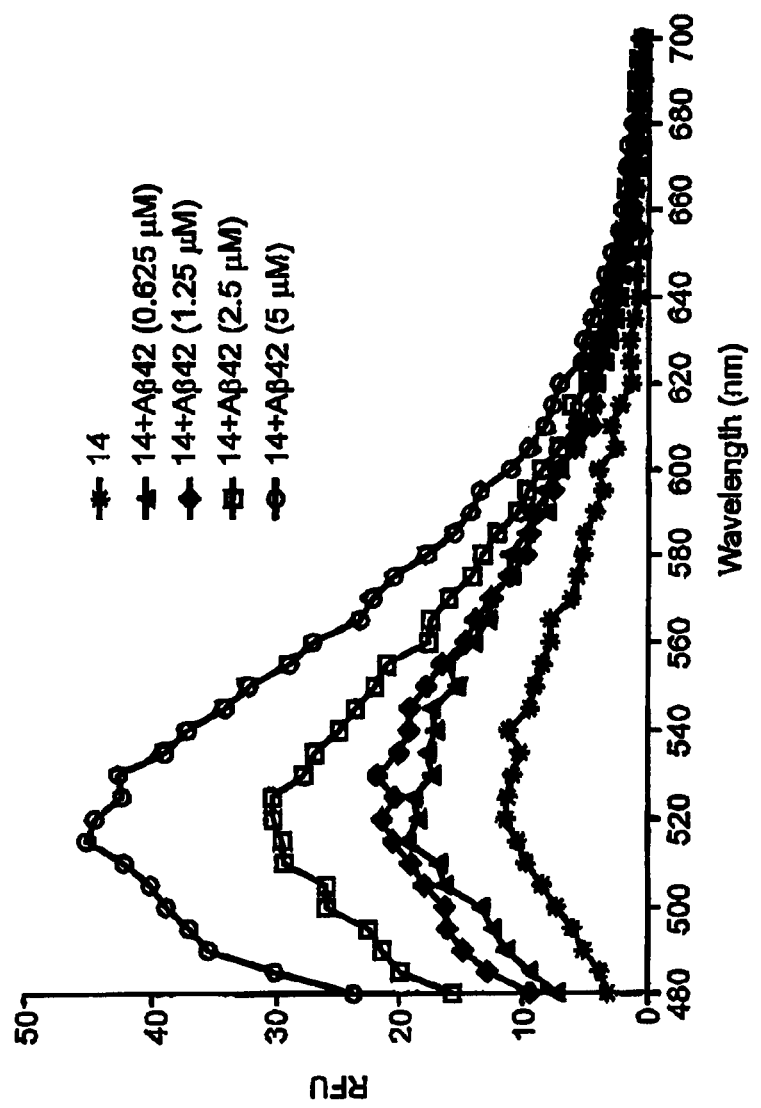
FIG. 9. Fluorescence emission of 14 (1 μM) before and after mixing with Aβ42 fibrils.

To examine the change of fluorescence properties upon binding to Aβ42, we compared the fluorescence properties of free 14 in aqueous solution to its fluorescence properties in the presence of Aβ42 fibrils as this chemical probe will be used to detect Aβ plaques. As shown in FIG. 9, upon binding to Aβ42 fibrils, the intensity of the emission spectra of 14 was significantly increased (4.5 fold at Aβ42=5 µM) with excitation of 430 nm. A blue shift in the emission spectra of 10 nm was also observed upon association with Aβ42 fibrils. Taken together, the results suggest that 14 possess the desired optical properties as a useful fluorescence probe.

Figure 10:
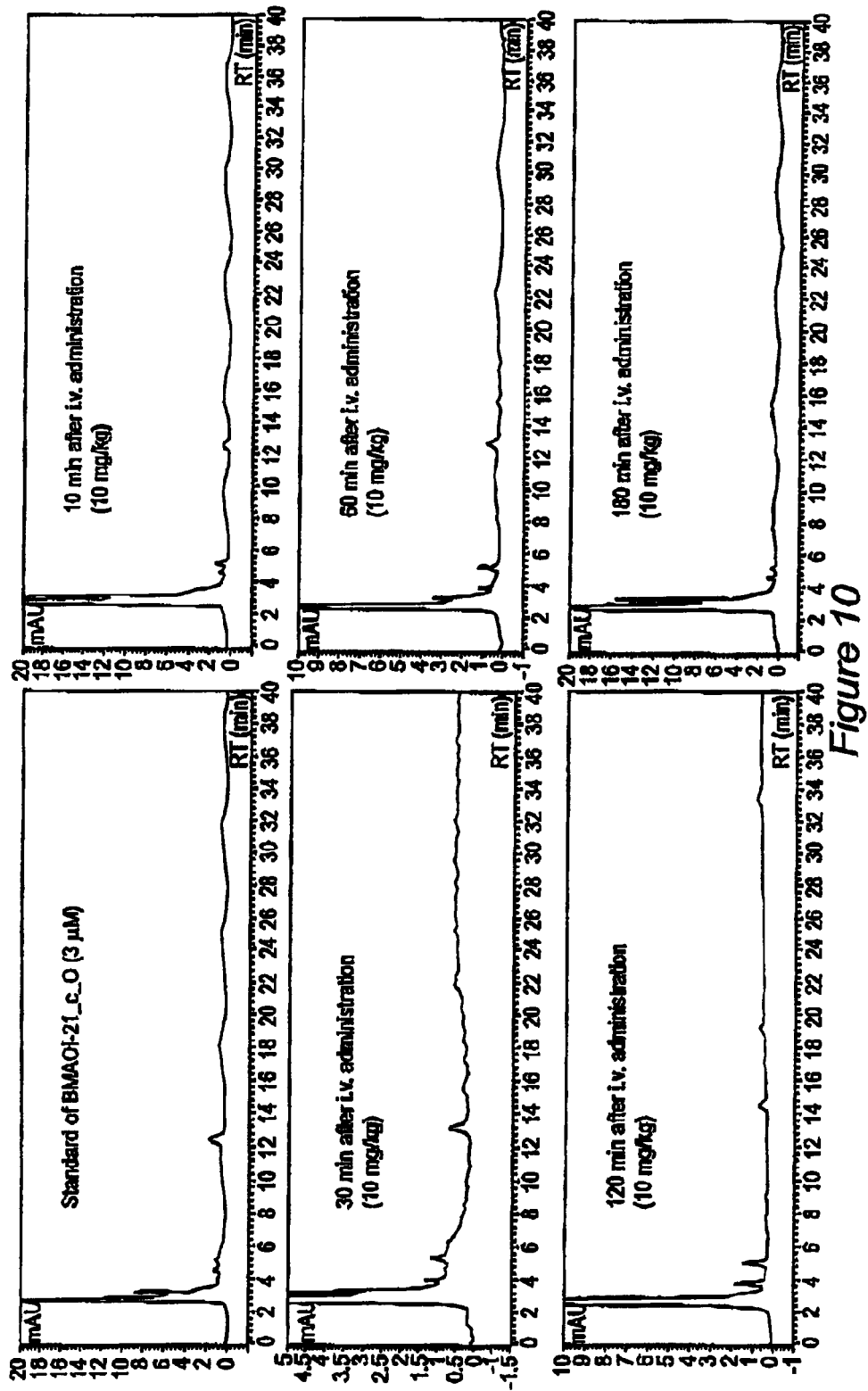
FIG. 10. Compound 14 can cross the blood brain barrier (BBB) of B6C3F1 mice. Compound 14 (10 mg/kg) was given to B6C3F1 female mice (n=3) by i.v. administration through tail-vein. Then the animals were sacrificed at indicated time intervals and the brain tissues were collected and analyzed by HPLC using C18 column.

An appropriate fluorescent probe must cross the BBB and selectively bind to Aβ plaques. Compound 14 has been shown to have the ability to cross the BBB in a caco-2 assay. Here, we further assessed the BBB permeability of 14 using female B6C3F1 mice combined with HPLC analysis. As shown in FIG. 10, 14 was detected in the brain tissue of B6C3F1 mice (n=3) at as early as 10 minutes after intravenous (i.v.) administration through the tail-vein of B6C3F1 mice (10 mg/kg dose). The presence of this compound in the brain tissue of B6C3F1 mice can last more than two hours as the detection is evident at 60 and 120 minutes, but disappears after 3 hrs of i.v. administration. The results may indicate that 14 can rapidly cross the BBB and reach the brain tissue and is metabolized in a reasonable time window (~3 hrs) that allows clinical operation. 14 appears to violate all of the empirical rules of BBB permeability with a molecule weight >1000 Da and being more lipophilic (log P>3). However, we also realize that there are exceptions and that compounds with molecular weight more than 1000 Da can efficiently cross the BBB and reach brain tissue. The in vivo experiment results also clearly demonstrate that this molecule efficiently and rapidly crosses the BBB. This is probably due to the unique structure of this probe as bivalent ligands containing cholesterol or cholesterylamine have been shown to efficiently cross the membrane system via internalization.

Figure 11B:
FIGS. 11A and B. Compound 14 stains the Aβ plaques in the brain tissues of TgCRND8 mice. A. The brain tissue of TgCRND8 mice was stained with 14 (10 μM) according to established protocol and viewed using confocal microscope; B. Adjacent section of the brain tissue was stained with anti-ADDL antibodies and viewed using confocal microscope.
Figure 11A:

Finally, in order to assess the binding ability of this compound to Aβ plaques, we stained sections of brain tissue derived from the cerebral cortex of TgCRND8 transgenic mouse, a widely used mouse model of AD. FIG. 11 represents examples of confocal micrographs of these tissue samples with 14 and specific Aβ antibodies anti-ADDL. As can be seen in FIG. 11A, 14 clearly stained Aβ plaques. The specific staining is confirmed by Aβ-specific antibody recognition in adjacent sections (FIG. 11B). Notably, 14 exhibits improved fluorescence contrast between the plaques and surrounding tissue even compared with specific anti-ADDL antibodies.

In summary, we demonstrate that a bivalent ligand containing curcumin and cholesterol, 14, can bind to various Aβ42 species with micromolar binding affinity and has appropriate fluorescence properties for labeling and imaging Aβ plaques. We also demonstrate that this chemical probe can rapidly cross the BBB and reach the brain tissue in B6C3F1 mice. In addition, this compound can be cleared out in a reasonable time window. Furthermore, 14 can stain nicely the Aβ plaques from the brain tissues of TgCRND8 transgenic mice with high contrast. Collectively, the results from this study suggest that 14 and this type of bivalent molecules hold the promise as fluorescent probes for Aβ-imaging. Further development and optimization of 14 as lead compound may provide useful diagnostic agents for AD.

Example 3

Second Generation BMAOIs

In the studies described in Example 1, a series of BMAOIs containing curcumin and cholesterol were designed, chemically synthesized and biologically assayed to reach the proof-of-concept of our BMAOI strategy. The results demonstrated that BMAOIs with optimal spacer length and connectivity localize to the CM/LR, efficiently suppress the production of intracellular Aβs, protect MC65 cells as well as retain the antioxidant and metal complexation activities. Furthermore, the lead BMAOI can cross the BBB and bind to the Aβ plaques. In order to further validate the BMAOI strategy and develop additional BMAOIs, a new series of BMAOIs containing cholesterylamine as the CM/LR anchorage moiety and curcumin as the multifunctional moiety were designed, synthesized and characterized. Cholesterylamine was chosen to replace cholesterol due to the following: 1) It has been reported that N-alkyl derivatives of cholesterylamine can also effectively anchor CM/LR in mammalian cells and function as carriers via endocytosis with improved activity copared to cholesterol.[73-76] This might be due to the H-bond interactions with CM/LR components through the —NH— moiety of cholesterylamine. 2) Replacement of cholesterol with cholesterylamine may reduce the concern of introducing additional cholesterol into the body as higher cholesterol level has been suggested to facilitate the development of AD even though the roles of cholesterol are still under debate.

Figure 12:
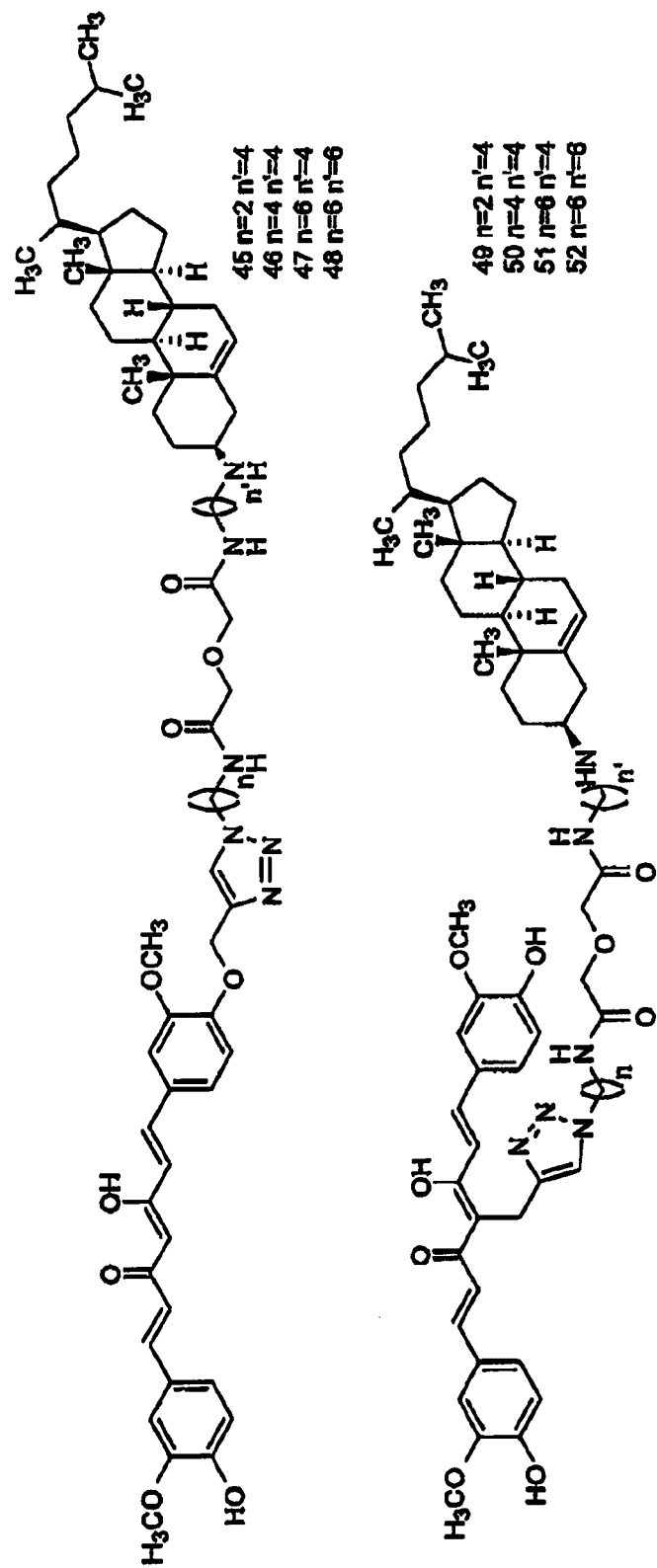
FIG. 12. Designed BMAOIs containing cholesterylamine as CM/LR anchorage moiety.

As shown in FIG. 12, a new series of BMAOIs with the spacer length varying from 17 to 23 atoms (compounds 45-52) were designed to further validate the BMAOI strategy. The objectives of designing this series of BMAOIs are to investigate 1) whether NH is preferred over O in the interaction with CM/LR; 2) whether spacer connectivity on 1 are still critical in this series of BMAOIs; and 3) whether the optimal spacer length to produce desired activity will still be within similar range as the first generation BMAOIs.

Chemical synthesis of 45-52 started with the synthesis of cholesterylamine 56 as shown in Scheme 4a. Briefly, cholesterol was reacted with methane sulfonyl chloride to afford 54, which was converted to 3β-azido-5-cholestene 55 by reacting with TMSN3 in the presence of BF3•Et20. 55 was then reduced to cholesterylamine 56 using lithium aluminum anhydride (LAH). Reaction of 56 with N-bromoalkyl-phthalimide in the presence of K2CO3 followed by Boc-protection of the 3β-NH afforded 57 and 58, respectively. Intermediates 57 and 58 were treated with hydrazine to afford 59 and 60, respectively. Coupling reaction of 59 or 60 with diglycolic anhydride followed by further coupling reactions with various azidoalkylamines yielded intermediates 61-64. Finally, click reactions of 20 or 23 with 61-64 followed by the removal of Boc afforded designed BMAOIs 45-52.

Scheme 4[a]

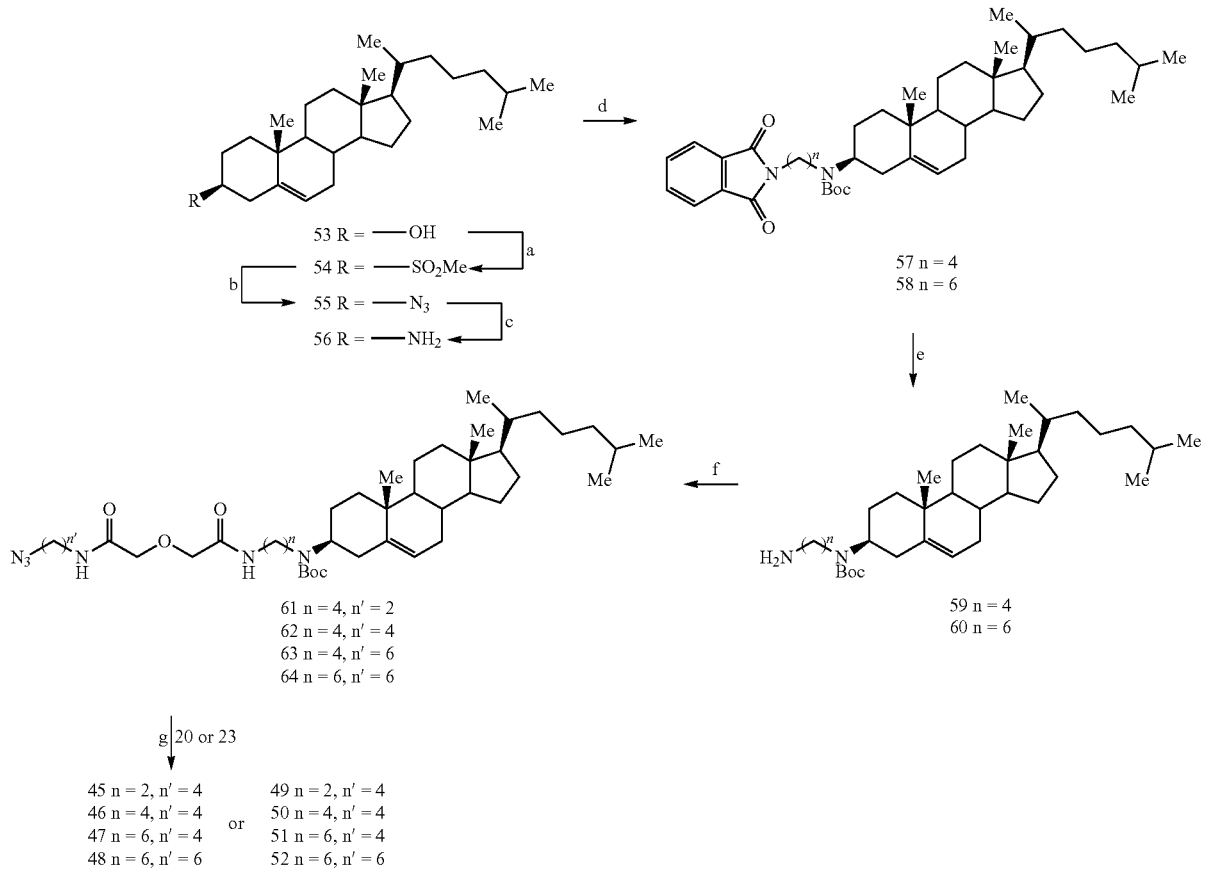

[a]Reagents and conditions: a) Mesyl chloride, Et₃N, DCM; b) TMSN₃, BF₃•O₂Et, DCM; c) LiAlH₄, Et₂O; d) i. N-(bromoalkyl)-phthalimide, K₂CO₃, DMF; ii. (Boc)₂O, DIEA, DCM; e) Hydrazine, EtOH; f) Diglycolic anhydride, TEA, DCM; f) various azidoalkylamines, EDCl, DIPA, DCM; g) i. Sodium ascorbate, CuSO₄, THF/H₂O (1:1); ii. TFA/DCM.

Results and Discussion.

Figure 13B:
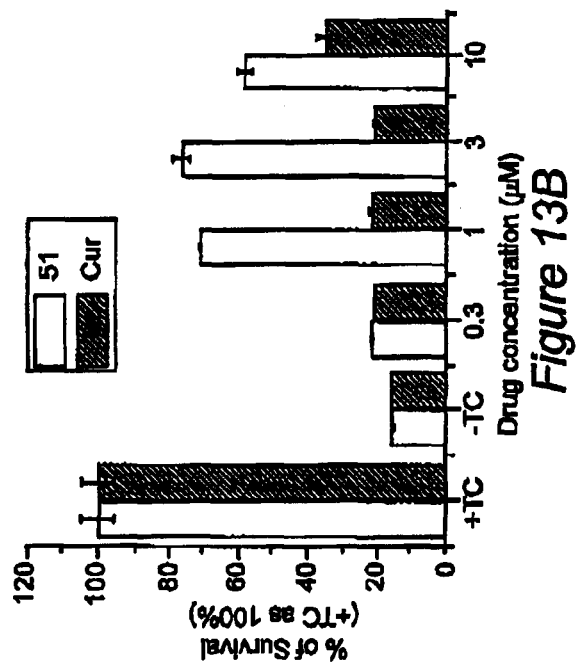
FIGS. 13A and B. Compound 51 protects MC65 cells from TC removal-induced cytotoxicity. A. MC65 cells were treated with indicated compounds at 10 μM under +TC or −TC conditions for 72 hrs. Cell viability was assayed by MTS assay. Data were expressed as mean percentage viability (n=6) with parallel +TC cultures set at 100% viability. Error bars represent SEM. B. MC65 cells were treated with 51 or curcumin at indicated concentrations and cell viability was analyzed as described in A.
Figure 13A:
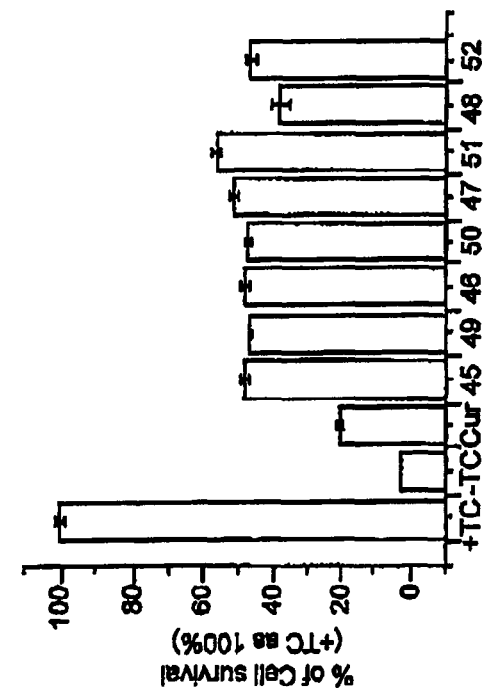

Neuroprotective effects of 45-52 in MC65 cells. After synthesis, these compounds were initially screened at 10 μM concentration for the protective activity in MC65 cells upon the removal of TC. As shown in FIG. 13A, all the compounds showed significant neuroprotective activity against the cytotoxicity induced by the removal of TC. Notably, among these BMAOIs, compound 51 exhibited the most potent protective activity in MC65 cells. More importantly, 51 has also a 21-atom spacer with the same spacer connectivity on curcumin 1 as compound 14. These results may indicate that the optimal spacer length in these two series of BMAOIs is within the same range with 21-atom spacer being the optimal one among the tested compounds and the replacement of cholesterol with cholesterylamine does not influence the spacer length and connectivity preference. Compound 51 was further confirmed to dose-dependently protect MC65 cells from TC removal-induced cytotoxicity with EC50 around 1.2 μM (FIG. 13B).

Figure 14A:
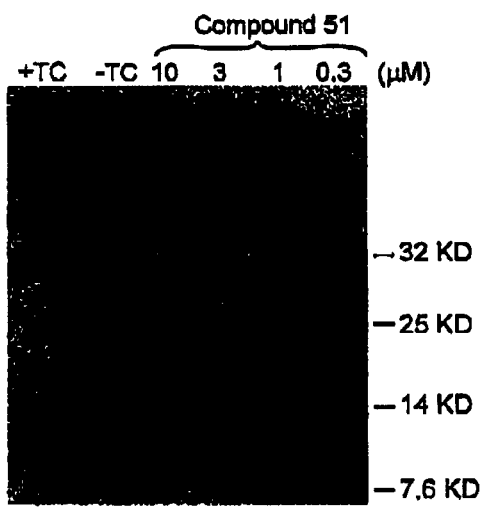
FIGS. 14A and B. Compound 51 inhibits the production of AβOs in MC65 cells and possess anti-oxidant activity. A. MC65 cells were treated with indicated compounds (10 μM) for 24 hrs immediately after the removal of TC. Lysates from cultures were analyzed by Western blotting using 6E10 antibody. The image represents the results from one of three independent experiments. B. MC65 cells were treated with 1 or 14 at indicated concentrations under +TC or −TC conditions for 24 hrs, then DCFH-DA (25 μM) was loaded and fluorescence intensity was analyzed at 485 nm (excitation) and 530 nm (emission). Data were presented as mean percentage of fluorescence intensity (n=5) with parallel −TC cultures set at 100%. Error bars represent SEM.

Compound 51 reduced the production of Aβ in MC65 cells. To confirm whether the neuroptective activity of 51 is related to the suppression of the production of AβOs, western blot analysis was performed in MC65 cells upon the treatment of 51. As shown in FIG. 14A, 51 dose-dependently inhibited the production of AβOs after the removal of TC in MC65 cells. This is consistent with the results of neuroprotective assays, thus indicating the neuroprotective activity of 51 is, at least partially, due to the inhibition of AβOs in MC65 cells. Taken together, these results further suggest that the interactions of BMAOIs with CM/LR can increase their potency and spacer length and attachment position on 1 are essential structural determinants for their biological activities.

Figure 14B:
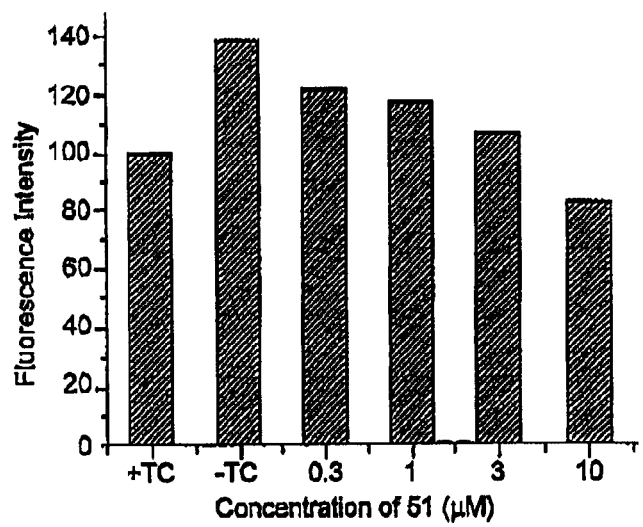

Compound 51 possesses anti-oxidant property. One of goals in the development of BMAOIs is to design compounds with intrinsic antioxidant activity; therefore 51 was evaluated for anti-oxidant effects using the DCFH-DA based cellular antioxidant assay in MC65 cells as described in Example 1. As shown in FIG. 14B, intracellular oxidative stress is significantly increased upon TC removal as reflected by the increased fluorescence intensity. Notably, 51 dose-dependently reduced the oxidative stress induced by the removal of TC and exhibited anti-oxidant activity even at as low as 3 μM concentration. Compound 51 even inhibited the basal oxidative stress level at higher concentration (10 μm). The results clearly suggest that compound 51 possesses anti-oxidant activity, which strongly supports the rationale of designing BMAOIs.

Conclusions

A series of BMAOIs with cholesterylamine as the CM/LR anchorage moiety were designed and biologically characterized. The spacer length in this new series of BMAOIs varies from 17 to 23 atoms. The results indicate that the preference for spacer length and connectivity is retained in this cholesterylamine series of BMAOIs. Compound 51 with a 21-atom spacer was identified to show neuroprotective activity against the AβO-induced cytotoxicity in MC65 cells. Compound 51 also exhibits anti-oxidant properties. Together, the results from this new series of BMAOIs further support and validate the proof-of-concept of the BMAOI strategy, thus attesting to the potential of this methodology in developing more potent BMAOIs to target the multiple risk factors involved in the pathology of AD.

Example 4

Curcumin-Melatonin Hybrid as the AβO-Inhibitor Moiety

Figure 15:
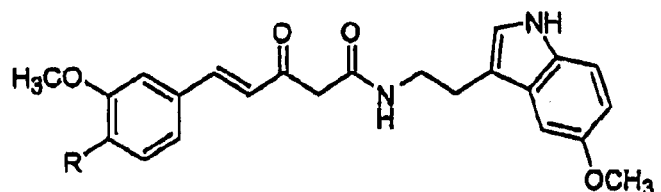
FIG. 15. Depiction of exemplary hybrid comprising curcumin and melatonin.

The structure of an exemplary curcumin-melatonin hybrid is shown in FIG. 15.

References
1. Hardy, J.; Selkoe, D., J. Science 2002, 297, 353-356.
2. Pratico, D., Trends Pharmacol. Sci. 2008, 29, 609-615.
3. Selkoe, D. J., Behay. Brain Res. 2008, 192, 106-113.
4. Lue, L. F.; Kuo, Y. M.; Roher, A. E.; Brachova, L.; Shen, Y.; Sue, L.; Beach, T.; Kurth, J. H.; Rydel, R. E.; Rogers, J. Am. J. Pathol. 1999, 155, 853-862,
5. McLean, C. A.; Cherny, R. A.; Fraser, F. W.; Fuller, S. J.; Smith, M. J.; Beyreuther, K.; Bush, A. I.; Masters, C. L., Ann. Neurol. 1999, 46, 860-866.
6. King, M. E.; Kan, H. M.; Baas, P. W.; Erisir, A.; Glabe, C. G.; Bloom, G. S., J. Cell Biol. 2006, 175, 541-546.
7. Zhang, Y.; McLaughlin, R.; Goodyer, C.; LeBlanc, A., J. Cell Biol. 2002, 156, 519-529.
8. Lal, R.; Lin, H.; Quist, A. P., Biochim. Biophys. Acta 2007, 1768, 1966-1975.
9. Green, K. N.; LaFeria, F. M., Neuron 2008, 59, 190-194.
10. Gasparini, L.; Dityatev, A., Exp. Neural. 2008, 212, 1-4.
11. Chafekar, S. M.; Baas, F.; Scheper, W., Biochim. Biophys, Acta 2008, 1782, 523-531.
12. Petersen, R. B.; Nunomura, A.; Lee, H. G.; Casadesus, G. Perry, G.; Smith, M. A.; Zhu, X., J. Alzheimer's Dis. 2007, 11, 143-152.
13. Reddy, P. H.; Beal, M. F., Trends Mol. Med. 2008, 14, 45-53.
14. Fukui, H.; Moraes, C. T., Trends Neurosci. 2008, 31, 251-256.
15. Cordy, J. M.; Hooper, N. M.; Turner, A., J. Mol. Membr. Biol. 2006, 23, 111-122.
16. Kim, S. I.; Yi, J. S.; Ko, Y. G., J. Cell. Biochem. 2006, 99, 878-889.
17. Choo-Smith, L. P.; Garzon-Rodriguez, W.; Glabe, C. G.; Surewicz, W. K., J. Biol. Chem. 1997, 272, 22987-22990.
18. Atwood, C. S.; Moir, R. D.; Huang, X.; Scarpa, R. C.; Bacarra, N. M.; Romano, D. M.; Hartshorn, M. A.; Tanzi, R. E.; Bush, A. L, J. Biol. Chem. 1998, 273, 12817-12826.
19. Wakabayashi, M.; Okada, T.; Kozutsumi, Y.; Matsuzaki, K., Biochem. Biophys. Res. Commun. 2005, 328, 1019-1023.
20. Wang, S. S.; Rymer, D I.; Good, T. A., J. Biol. Chem. 2001, 276, 42027-42034.
21. Ariga, T.; McDonald, M. P.; Yu, R. K., J. Lipid Res. 2008, 49, 1157-1175.
22. Oda, A.; Tamaoka, A.; Araki, W., J. Neurosci. Res. 2010, 88, 1137-1145.
23. Panza, F.; Solfrizzi, V; Frisardi, V; Imbimbo, B. P.; Capurso, C.; D'Introno, A.; Colacicco, A. M.; Seripa, D.; Vendemiale, G.; Capurso, A.; Pilotto, A., Aging Clin. Exp. Res. 2009, 21, 386-406.
24. Sabbagh, M. N., Am. J. Geriatr. Pharmacother. 2009, 7, 167-185.
25. Cavalli, A.; Bolognesi, M. L.; Minarini, A.; Rosini, M.; Tumiatti, V.; Recanatini, M.; Melchiorre, C., J. Med. Chem. 2008, 51, 347-372.
26. Amit, T.; Avramovich-Tirosh, Y.; Youdium, M. B.; Mandel, S. FASEB J. 2008, 22, 1296-1305.
27. Kim, Y. S.; Lee, J. H.; Rya, J.; Kim, D. J., Curr. Pharm. Des. 2009, 15, 637-658.
28. Portoghese, P. S. J., Med. Chem. 2001, 44, 2259-2269.
29. Yang, F.; Lim, G. P.; Begum, A. N.; Ubeda, O. J.; Simmons, M. R.; Ambegaokar, S. S.; Chen, P. P.; Kayed, R.; Glabe, C. G.; Frautschy, S. A.; Cole, G. M., J. Biol. Chem. 2005, 280, 5892-5901.
30. Ray, B.; Lahiri, D. K., Curr. Opin. Pharmacol. 2009, 9, 434-444.
31. Frautschy, S. A.; Cole, G. M., Mol. Neurobiol. 2010, 41, 392-409.
32. Kim, J.; Lee, H. J.; Lee, K. W., J. Neurochem. 2010, 112, 1415-1430.
33. Rajendran, L.; Schneider, A.; Schlechtingen, G.; Weidlich, S.; Ries, J.; Braxmeier, T.; Schwille, P.; Schulz, J. B.; Schroeder, C.; Simons, M.; Jennings, G.; Knolker, H. J.; Simons, K., Science 2008, 320, 520-523.
34. Hussey, S. L.; He, E.; Peterson, B. R., Org. Lett. 2002, 4, 415-418.
35. Kolb, H. C.; Sharpless, K. B., 2003, 8, 1128-1137.
36. Ouberai, M.; Dumy, P.; Chierici, S.; Garcia, J., Bioconjugate Chem. 2009, 20, 2123-2132.
37. Pabon, H. J. J., Rec. Tray. Chim. 1964, 83, 379-386.
38. Sopher, B. L.; Fukuchi, K.; Smith, A. C.; Leppig, K. A.; Furlong, C. E.; Martin, G. M., Brain Res. Mol. Brain Res. 1994, 26, 207-217.
39. Maezawa, 1.; Hong, H. S.; Wu, H. C.; Battina, S. K.; Rana, S.; Iwamoto, T.; Radke, G. A.; Petterson, E.; Martin, G. M.; Hua, D. H.; Jin, L. W., J. Neurochem. 2006, 98, 57-67. 40. Sopher, B. L.; Fukuchi, K.1.; Kavanagh, T. J.; Furlong, C. E.; Martin, G. M., Mol. Chem. Neuropathol. 1996, 29, 153-167.
41. Xia, W.; Zhang, J.; Kholodenko, D.; Citron, M.; Podlisny, M. B.; Teplow, D. B.; Haass, C.; Seubert, P.; Koo, E. H.; Selkoe, D. J., J. Biol. Chem. 1997, 272, 7977-7982.
42. Walsh, D. M.; Tseng, B. P.; Rydel, R. E.; Podlisny, M. B.; Selkoe, D. J., Biochemistry 2000, 39, 10831-10839.
43. Kayed, R.; Head, E.; Thompson, J. L.; McIntire, T. M.; Milton, S. C.; Cotman, C. W.; Glade, C. G., Science 2003, 18, 486-489.
44. Lantto, T. A.; Colucci, M.; Zavadova, V.; Hiltunen, R.; Raasmaja, A., Food Chem. 2009, 117, 405-411.
45. Oyama, Y.; Hayashi, A.; Ueha, T.; Maekawa, K., Brain Res. 1994, 635, 113-117.
46. Forrest, V. J.; Kang, Y. H.; McClain, D. E.; Robinson, D. H.; Ramakrishnan, N., Free Radical. Biol. Med. 1994, 16, 675-684.
47. Woltjer, R. L.; Nghiem, W.; Maezawa, I.; Milatovic, D.; Vaisar, T.; Montine, K. S.; Montine, T. J., J. Neurochem. 2005, 93, 1047-1056.
48. Adachi Y.; Suzuki, H; Sugiyama, Y., Pharm. Res. 2001, 18, 1660-1668.
49. Mensch, J.; Melis, A.; Mackie, C.; Verreck, G.; Brewster, M. E.; Augustijns, P., Eur. J. Pharm. Biopharm. 2010, 74, 495-502.
50. Garberg, P.; Ball, M.; Borg, N.; Cecchelli, R.; Fenart, L.; Hurst, R. D.; Lindmark, T.; Mabondzo, A.; Nilsson, J. E.; Raub, T. J.; Stanimirovic, D.; Terasaki, T.; Oberg, J. O.; Osterberg, T., Toxicol. In Vitro 2005, 19, 299-334.
51. Poller, B.; Gutmann, H.; Krahenbuhl, S.; Weksler, B.; Romero, I.; Couraud, P. O.; Tuffin, G.; Drewe, J.; Huwyler, J., J. Neurochem. 2008, 107, 1358-1368.

52. Lohmann, C.; Huwel, S.; Galla, H. J., J. Drug Target 2002, 10, 263-276.
53. Usta, M.; Wortelboer, H. M.; Vervoort, J.; Boersma, M. G.; Rietjens, I. M.; van Bladeren, P. J.; Cnubben, N. H., Chem. Res. Toxicol. 2007, 20, 1895-1902.
54. Giacomini, K. M.; Huang, S. M.; Tweedie, D. J.; Benet, L. Z.; Brouwer, K. L.; Chu, X.; Dahlin, A.; Evers, R.; Fischer, V.; Hillgren, K. M.; Hoffmaster, K. A.; Ishikawa, T.; Keppler, D.; Kim, R. B.; Lee, C. A.; Niemi, M.; Polli, J. W.; Sugiyama, Y.; Swaan, P. W.; Ware, J. A.; Wright, S. H.; Wah Yee, S.; Zamek-Gliszczynski, M. J.; Zhang, L., Nat. Rev. Drug Discov. 2010, 9, 215-236.
55. Wang, Y. J.; Thomas, P.; Zhong, J. H.; Bi, F. F.; Kosaraju, S.; Pollard, A.; Fenech, M.; Zhou, X. F., Neurotox. Res. 2009, 15, 3-14.
56. Garcia-Alloza, M.; Borrelli, L. A.; Rozkalne, A.; Hyman, B. T.; Bacskai, B. J., J. Neurochem. 2007, 102, 1095-1104.
57. Ryu, E. K.; Choe, Y. S.; Lee, K. H.; Choi, Y.; Kim, B. T., J. Med. Chem. 2006, 49, 6111-6119.
58. Zamrini, E.; De Santi, S.; Tolar, M., Neurobiol. Aging 2004, 25, 685-691.
59. Higuchi, M., Iwata, N., Matsuba, Y., Sato, K., Sasamoto, K., and Saido, T. C. (2005) Nat. Neurosci. 8, 527-533
60. Poduslo, J. F., Curran, G. L., Peterson, J. A., McCormick, D. J., Fauq, A. H., Khan, M. A., and Wengenack, T. M. (2004) Biochemistry 43, 6064-6075
61. Garcia-Alloza, M., Borrelli, L. A., Rozkalne, A., Hyman, B. T. and Bacskai, B. J. (2007) J. Neurochem. 102, 1095-104
62. D'Amore, J. D., Kajdasz, S. T., McLellan, M. E., Bacskai, B. J., Stern, E. A. and Hyman, B. (2003) J. Neuropathol. Exp. Neurol. 62, 137-45
63. Hintersteiner, M., Enz, A., Frey, P., Jaton, A.-L., Kinzy, W., Kneuer, R., Neumann, U., Rudin, M., Staufenbiel, M., Stoeckli, M., Wiederhold, K.-H., and Gremlich, H.-U. (2005 Nat. Biotechnol. 23, 577-583
64. Nesterov, E. E., Skoch, J., Hyman, B. T., Klunk, W. E., Bacskai, B. J., and Swager, T. M. (2005) Angew. Chem., Int. Ed. 44, 5452-5456
65. Sutharsan, J., Dakanali, M., Capule, C. C., Haidekker, M. A., Yang, J., and Theodorakis, E. A. (2010) Chem Med Chem 5, 56-60
66. Ran, C., Xu, X., Raymond, S. B., Ferrara, B. J., Neal, K., Bacskai, B. J., Medarova, Z., and Moore, A. (2009) J. Am. Chem. Soc. 131, 15257-15261
67. Chang, W. M., Dakanali, M., Capule, C. C., Sigurdson, C. J., Yang J., and Theodorakis, E. A. (2011) ACS Chem. Neurosci. 2, 249-25568. Raymond, S. B., Skoch, J., Hills, I. D., Nesterov, E. E., Swager, T. M., and Bacskai, B. J. (2008) Eur. J. Nucl. Med. Mol. Imaging 35 (suppl. 1) 93-98
69. Li, Q., Lee, J. S., Ha, C., Chan, B. P., Yang, G., Wen, B. G., and Chang, Y. T. Angew. Chem., Int. Ed. 2004, 43, 6331-6335.
70. Ono, M., Ishikawa, M., Kimura, H., Hayashi, S., Matsumura, K., Watanabe, H., Shimizu, Y., Cheng, Y., Cui, M., Kawashima, H., and Saji, H. Bioorg. Med. Chem. 2010, 20, 3885-3888.
71. Lenhart J A, Ling X, Gandhi R, Guo T L, Gerk P M, Brunzell D H, Zhang S. J. Med. Chem. 2010, 53, 6198-6209.
72. Ryu, E. K.; Choe, Y. S.; Lee, K. H.; Choi, Y.; Kim, B. T. J. Med. Chem. 2006, 49, 6111-6119.
73. Hussey, S. L.; He, E.; Peterson, B. R., J. Am. Chem. Soc. 2001, 123, 12712-12713.
74. Boonyarattanakalin, S.; Martin, S. E.; Dykstra, S. A.; Peterson, B. R., J. Am. Chem. Soc. 2004, 126, 16379-16386.
75. Hussey, S. L.; Peterson, B. R., J. Am. Chem. Soc. 2002, 124, 6265-6273.
76. Barragan, V.; Menger, F. M.; Caran, K. L.; Vidil, C.; Morere, A.; Montero, J.-L., Chem. Commun. 2001, 85-86.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A bivalent multifunctional AP oligomerization inhibitor (BMAOI) comprising
   i) curcumin;
   ii) a cell membrane/lipid raft (CM/LR) anchor selected from the group consisting of cholesterol, cholesterylamine, and diosgenin; and
   iii) a spacer moiety which forms a chemical linkage between said curcumin and said CM/LR anchor, wherein said spacer moiety is 17-39 atoms in length.

2. The BMAOI of claim 1, wherein said spacer moiety is 21 atoms in length.

3. The BMAOI of claim 1, wherein said spacer moiety is chemically linked to carbon at position C4 of said curcumin.

4. The BMAOI of claim 1, wherein said CM/LR anchor is cholesterol and said spacer moiety is chemically linked to O attached to position C3 of said cholesterol.

5. The BMAOI of claim 1, wherein said CM/LR anchor is cholesterylamine and said spacer moiety is chemically linked to N attached to position C3 of said cholesterylamine.

6. A method of treating Alzheimer's disease (AD) in a patient in need thereof, comprising the step of
   administering to said patient a bivalent multifunctional Aβ oligomerization inhibitor (BMAOI) comprising
   i) curcumin;
   ii) a cell membrane/lipid raft (CM/LR) anchor selected from the group consisting of cholesterol, cholesterylamine, and diosgenin; and
   iii) a spacer moiety which forms a chemical linkage between said curcumin and said CM/LR anchor, wherein said spacer moiety is 17-39 atoms in length, wherein said BMAOI is administered in an amount sufficient to treat said AD in said patient.

7. The method of claim 6, wherein said bivalent multifunctional ligand is compound 14,

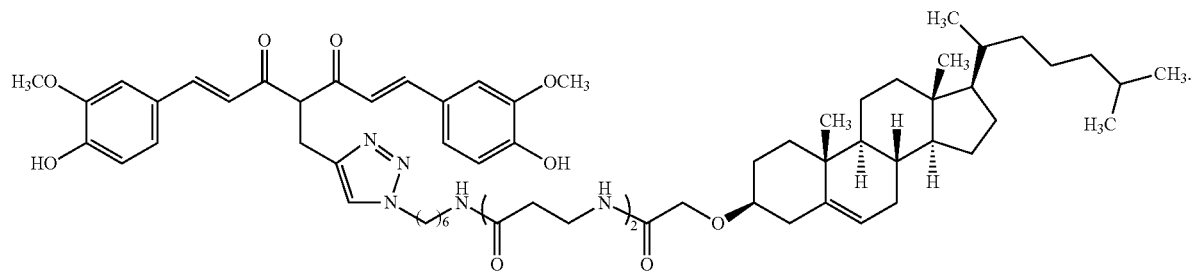

14

8. The method of claim 6, wherein said bivalent multifunctional ligand is compound 51,

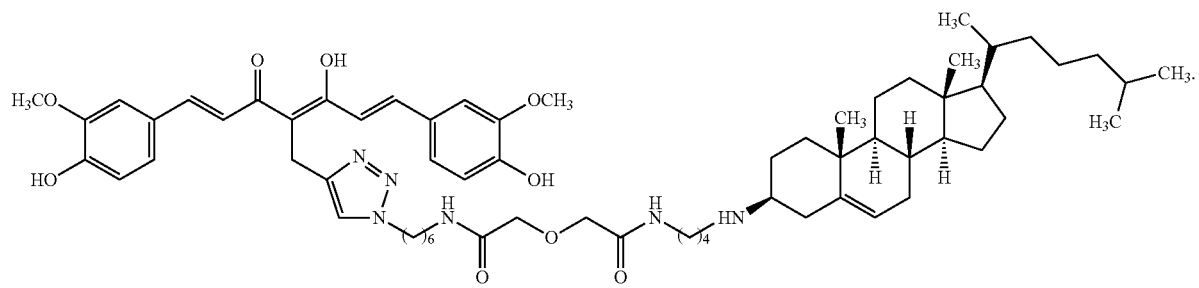

51

9. A method of imaging or visualizing β-amyloid (Aβ) plaques in brain tissue, comprising the steps of
 exposing said brain tissue to at least one bivalent multifunctional Aβ oligomerization inhibitor (BMAOI) comprising
  i) curcumin;
  ii) a cell membrane/lipid raft (CM/LR) anchor selected from the group consisting of cholesterol, cholesterylamine, and diosgenin; and
  iii) a spacer moiety which forms a chemical linkage between said curcumin and said CM/LR anchor, wherein said spacer moiety is 17-39 atoms in length, and wherein said step of exposing is carried out under conditions that allow said at least one BMAOI to associate with said AP plaques in said brain tissue;
 exposing said brain tissue to a source of electromagnetic radiation; and
 detecting fluorescence emitted from BMAOIs associated with said Aβ plaques.

10. The method of claim 9, wherein said bivalent multifunctional ligand is compound 14,

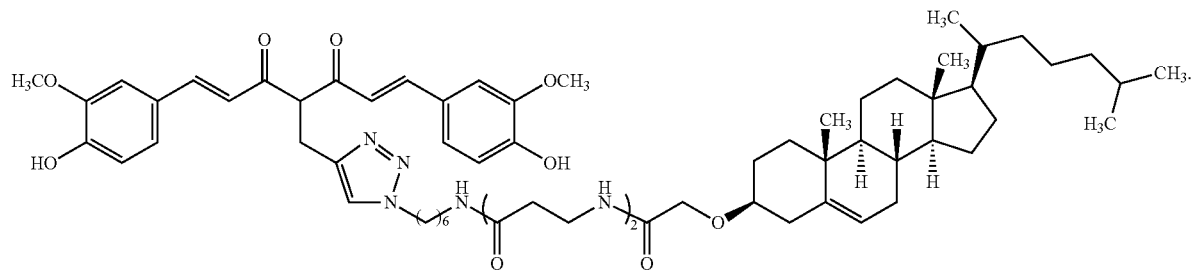

14

11. The method of claim 9, wherein said bivalent multifunctional ligand is compound 51,
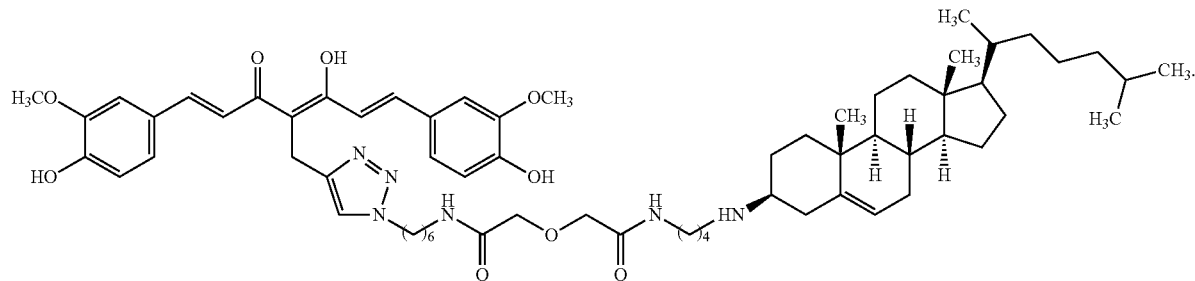
12. The BMAOI of claim 1, wherein said spacer moiety includes at least one of a polyamine, a polyethylene glycol, and an amide.
* * * * *